(12) United States Patent
    Subbian

(10) Patent No.: US 10,190,101 B2
(45) Date of Patent: Jan. 29, 2019

(54) PRODUCTION OF LACTIC ACID FROM ORGANIC WASTE OR BIOGAS OR METHANE USING RECOMBINANT METHANOTROPHIC BACTERIA

(71) Applicant: STRING BIO PRIVATE LIMITED, Malleswaram, Bangalore (IN)

(72) Inventor: Ezhilkani Subbian, Bangalore (IN)

(73) Assignee: STRING BIO PRIVATE LIMITED, Malleswaram, Bangalore (IN)

( * ) Notice: Subject to any disclaimer, the term of this patent is extended or adjusted under 35 U.S.C. 154(b) by 0 days.

(21) Appl. No.: 15/303,188

(22) PCT Filed: Apr. 13, 2015

(86) PCT No.: PCT/IN2015/000168
§ 371 (c)(1),
(2) Date: Oct. 10, 2016

(87) PCT Pub. No.: WO2015/155790
PCT Pub. Date: Oct. 15, 2015

(65) Prior Publication Data
US 2017/0114331 A1    Apr. 27, 2017

(30) Foreign Application Priority Data
Apr. 11, 2014    (IN) .......................... 1901/CHE/2014

(51) Int. Cl.
*C12N 1/00*    (2006.01)
*C12P 7/56*    (2006.01)
(Continued)

(52) U.S. Cl.
CPC ............. *C12N 9/0006* (2013.01); *C12N 1/00* (2013.01); *C12N 15/74* (2013.01); *C12P 7/56* (2013.01); *C12Y 101/01027* (2013.01)

(58) Field of Classification Search
None
See application file for complete search history.

(56) References Cited

U.S. PATENT DOCUMENTS

| 5,527,464 A | 6/1996 | Bartha et al. |
| 2003/0166174 A1 | 9/2003 | Ono et al. |

(Continued)

FOREIGN PATENT DOCUMENTS

| WO | WO 2013/066848 A1 | 5/2013 |
| WO | WO 2014/009435 A1 | 1/2014 |

(Continued)

OTHER PUBLICATIONS

U.S. Appl. No. 61/928,390, filed Jan. 16, 2014, Specification, Claims, Abstract and Drawings.*

(Continued)

*Primary Examiner* — Richard C Ekstrom
(74) *Attorney, Agent, or Firm* — Foley & Lardner LLP

(57) ABSTRACT

The present disclosure provides for production of lactic acid from organic waste or biogas or methane using recombinant methanotrophic bacteria. In one embodiment, the recombinant methanotrophic bacterium includes a heterologous nucleic acid encoding for lactate dehydrogenase (ldh) enzyme. In a further embodiment, the capacity of the recombinant methanotrophic bacterium for producing lactic acid over basal level is increased by overexpression or/and down-regulation or deletion of specified genes. In another embodiment, a process for producing lactic acid from organic waste using the recombinant methanotrophic bacterium is disclosed. The present disclosure provides a cradle to cradle environment-friendly and commercially viable solution for managing organic waste.

12 Claims, 7 Drawing Sheets
Specification includes a Sequence Listing.

(51) Int. Cl.
*C12N 9/04* (2006.01)
*C12N 15/74* (2006.01)

(56) References Cited

U.S. PATENT DOCUMENTS

2004/0147011 A1  7/2004 Koffas et al.
2013/0224804 A1  8/2013 Knight
2016/0369246 A1* 12/2016 Saville ................ C12N 9/0006

FOREIGN PATENT DOCUMENTS

WO  WO 2014/066670 A1  5/2014
WO  WO 2014/165763 A1  10/2014
WO  WO 2014/205146 A1  12/2014

OTHER PUBLICATIONS

Geneseq Accession No. ATS61737, published Jan. 8, 2009.*
GenBank Accession No. AAU91299.1, published Nov. 21, 2011.*
International Search Report issued in PCT/IN15/00168 dated Dec. 22, 2015.

* cited by examiner

PRODUCTION OF LACTIC ACID FROM ORGANIC WASTE OR BIOGAS OR METHANE USING RECOMBINANT METHANOTROPHIC BACTERIA

CROSS-REFERENCE TO RELATED APPLICATIONS

The present application is a U.S. National Phase Application of International Patent Application No. PCT/IN2015/000168, filed Apr. 13, 2015, which claims priority to Indian Patent Application No. 1901/CHE/2014, filed Apr. 11, 2014, the entireties of which are incorporated herein by reference.

SEQUENCE LISTING

The instant application contains a Sequence Listing which has been submitted electronically in ASCII format and is hereby incorporated by reference in its entirety. Said ASCII copy, created on Dec. 7, 2016, is named 056859-0277_SL.txt and is 71,702 bytes in size.

FIELD OF THE INVENTION

The present disclosure relates to the field of waste management, and more particularly relates to converting organic waste to lactic acid by employing recombinant methanotrophic bacteria.

BACKGROUND OF THE INVENTION

Most modern cities are battling with increasing amount of garbage/waste generated and accumulated on a daily basis. Effective ways of managing the waste has become indispensable for maintaining sanitation and general quality of urban life. Sustainable and innovative solutions for managing waste are a critical need.

There are various modes of waste disposal known to us such as landfills, incineration, recycling, biological reprocessing etc. The most acceptable and sustainable modes of waste management are recycling and reprocessing for resource and energy recovery. In recycling, materials generally undergo a chemical transformation and resultant products are recycled to be used for various purposes. For the purpose of resource recovery the organic waste is preferably anaerobically digested (also called Anaerobic Composting or Biomethanation) as compared to aerobic digestion to obtain compost which can be used as an organic fertilizer on agricultural fields. Anaerobic digestion of organic waste results in energy in the form of biogas, and compost in the form of a liquid residual. The biogas consists of methane and carbon dioxide and can be used as fuel or, by using a generator, it can be converted to electricity on-site. This reduces greenhouse gas emissions by using methane as an energy source which would otherwise be emitted from landfilling waste. Landfilling waste gas is similar in composition to biogas with lower amount of methane and differences in component gases. However, the conversion of biogas to electricity is not economically attractive and also results in significant loss of energy during conversion.

Methane, present in biogas or landfill gas, can also be converted to syngas and then to chemicals such as methanol. This gas to liquid conversion, however, happens at high temperature and pressure necessitating huge capital investments. Efficient utilization of biogas as well as methane has always been a challenging task.

Advances in biotechnology are enabling development of new and improved microorganisms for efficient degradation of biomass. However, the existing state of the art does not provide for a unified and efficient way of converting organic wastes and more specifically biogas or methane to target chemicals by employing recombinant microorganisms.

SUMMARY OF THE INVENTION

The present disclosure overcomes above mentioned drawbacks by developing recombinant methanotrophic bacteria for converting organic waste to lactic acid and providing method of using the recombinant microorganisms for converting organic waste and specifically biogas and methane to lactic acid thereby providing an environment-friendly and commercially viable solution for waste management.

In one aspect of the present invention, a recombinant methanotrophic bacterium capable of producing lactic acid from organic waste or biogas or methane is provided. The recombinant methanotrophic bacterium includes a heterologous nucleic acid or gene encoding for lactate dehydrogenase (ldh) enzyme which is selected from sequences set forth as SEQ ID NOs.1, 3, 5, or a combination thereof.

In further aspect of the present invention, the recombinant methanotrophic bacterium with increased capacity of producing lactic acid over basal level is provided. The recombinant methanotrophic bacterium further includes gene(s) encoding enzyme(s) which are overexpressed, down-regulated or deleted or any combination thereof for increasing production of the lactic acid.

In another aspect of the present invention, a process for producing lactic acid from organic waste using the recombinant methanotrophic bacterium is provided. The said process includes steps of receiving organic waste as input, anaerobically digesting the organic waste to biogas, culturing the bacterium in the biogas so generated thereby converting the biogas to the lactic acid, and optionally purifying or separating the lactic acid produced from the culture for obtaining the lactic acid.

In yet another aspect of the present invention, an alternative process for producing lactic acid from a carbon source using recombinant methanotrophic bacterium is provided. The said process includes steps of receiving biogas and/or methane as carbon source as input, culturing the bacterium in the input, thereby converting the input into lactic acid, and optionally purifying or separating the lactic acid produced from the culture for obtaining the lactic acid.

Other features of the embodiments will be apparent from the accompanying drawings and from the detailed description that follows.

BRIEF DESCRIPTION OF THE ACCOMPANYING DRAWINGS

Figure 3:
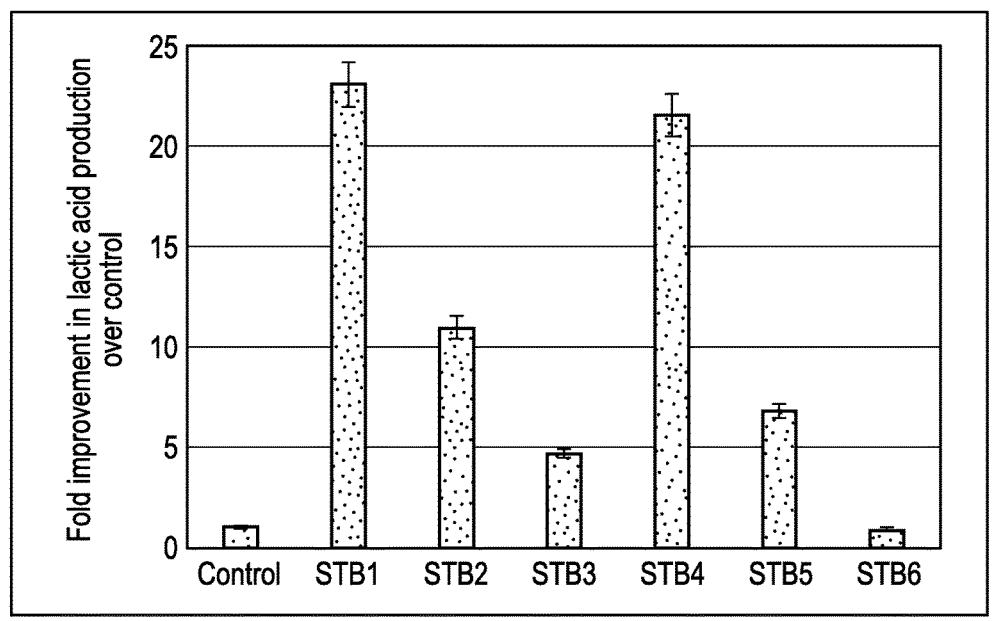

FIG. 3 is a graph illustrating conversion of methane to lactic acid in recombinant methanotroph strains. The graph highlights the fold improvement in lactic acid production in tested strains compared to control. Control—wildtype M. capsulatus; STB1/STB4—M. capsulatus with E. coli ldh cloned under sigma 70 and PmxaF; STB2/STB5—*M. capsulatus* with *P. aeruginosa* ldh under sigma 70 and PmxaF; STB3/STB6—*M. capsulatus* with *P. carotovorum* ldh under sigma 70 and PmxaF.

Figure 4:
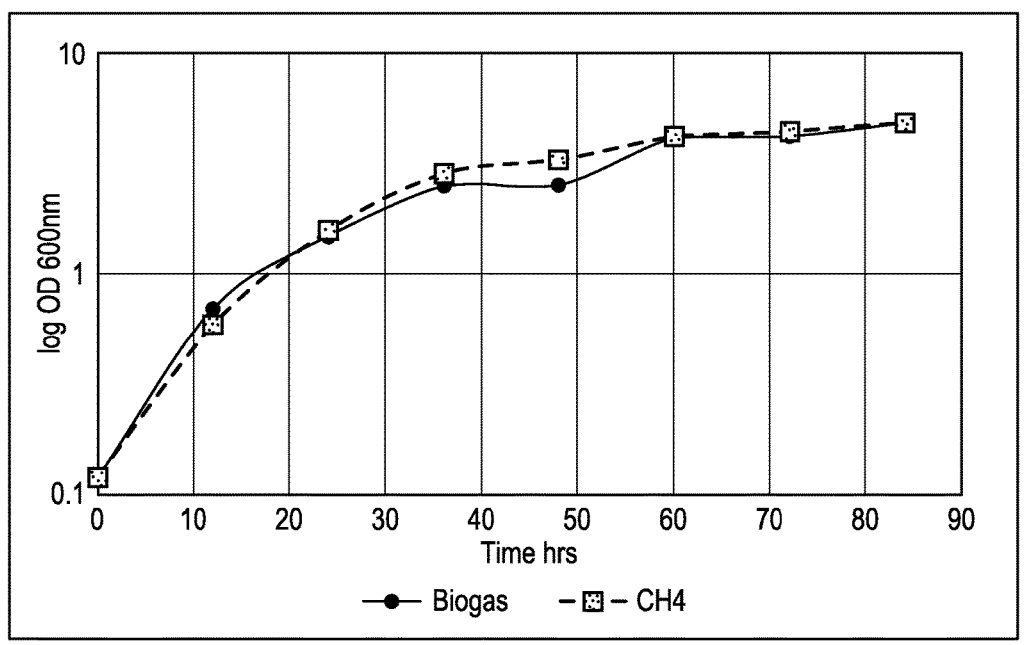

FIG. 4 is a graph illustrating comparative growth profile of methanotroph strain on Biogas and Methane.

Figure 5:
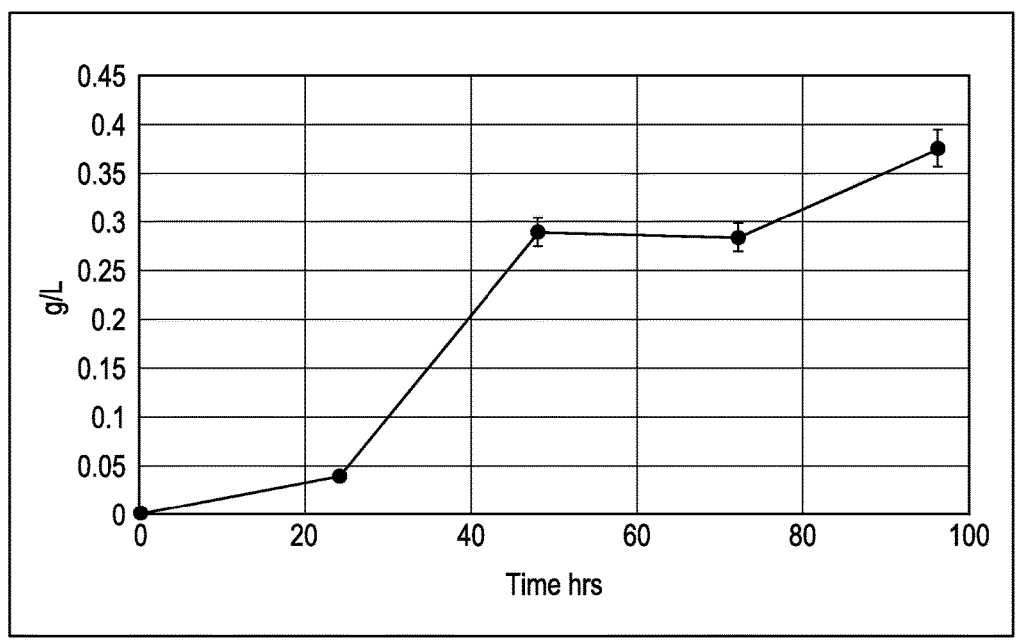

FIG. 5 is a graph illustrating conversion of biogas, generated from organic waste, to lactic acid using recombinant methanotroph strains with expressed lactate dehydrogenase. Increase in lactic acid production as a function of time is shown.

Figure 6:
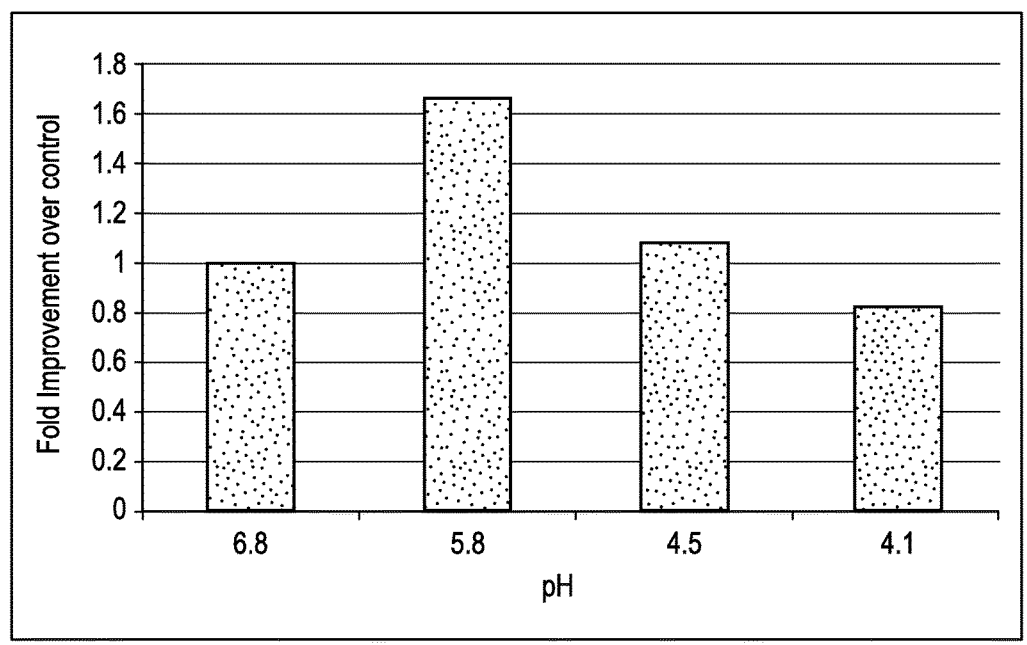

FIG. 6 is a graph depicting effect of pH on conversion of methane to lactic acid using recombinant methanotroph strains.

Figure 7:
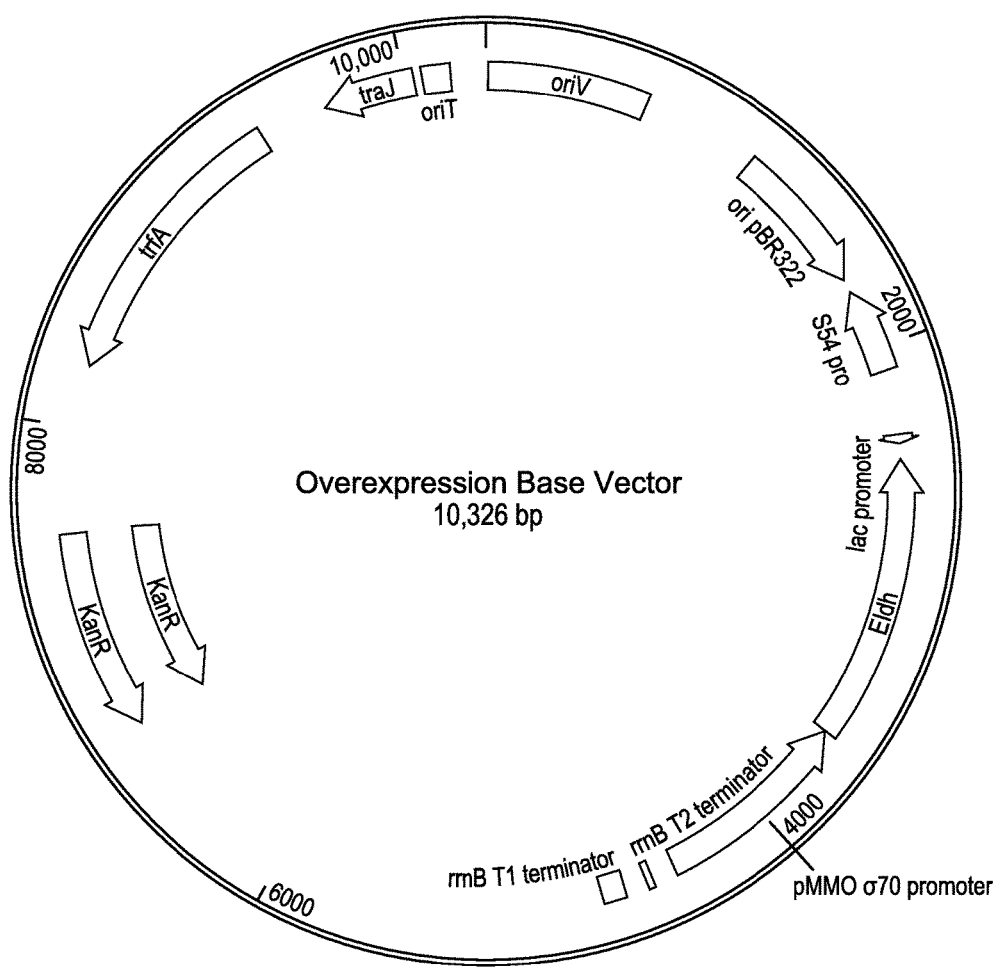

FIG. 7 illustrates a shuttle vector for gene overexpression for improved lactic acid production, according to one embodiment.

DEPOSIT OF MICROORGANISM

The following microorganism has been deposited in accordance with the terms of the Budapest Treaty with the Microbial Type Culture Collection and Gene Bank (MTCC), Chandigarh, India:

| Identification ref. | Taxonomic designation | MTCC Accession number |
|---|---|---|
| STB31 | *Methylococcus capsulatus* | MTCC 25006 |

The recombinant *Methylococcus capsulatus* capable of converting methane to lactic acid was deposited as MTCC Accession No.: MTCC 25006 on Jan. 27, 2015 with the Microbial Type Culture Collection and Gene Bank (MTCC), Institute of Microbial Technology, Sector 39-A, Chandigarh—160036, INDIA. The MTCC issued an accession number in this matter on Mar. 26, 2015. STB31 refers to the recombinant *Methylococcus capsulatus* strain that has the heterologous lactate dehydrogenase gene (SEQ ID 1) expressed from pSB102. This deposit was made under the provisions of the Budapest Treaty on the International Recognition of the Deposit of Microorganisms for the Purposes of Patent Procedure and the Regulations thereunder (Budapest Treaty). Availability of the deposited strain is not to be construed as a license to practice the invention in contravention of the rights granted under the authority of any government in accordance with its patent laws.

DETAILED DESCRIPTION OF THE INVENTION

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein/nucleic acid chemistry and hybridization described herein are those well-known and commonly used in the art. Certain references and other documents cited herein are expressly incorporated herein by reference. In case of conflict, the present specification, including definitions, will control. The materials, methods, and examples are illustrative only and not intended to be limiting.

Before the present vectors, genomes, bacteria, microbes, compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "comprising" as used herein is synonymous with "including" or "containing," and is inclusive or open-ended and does not exclude additional, unrecited members, elements or method steps.

The term "polynucleotide", "nucleic acid molecule", "nucleic acid", or "nucleic acid sequence" refers to a polymeric form of nucleotides of at least 10 bases in length. The term includes DNA molecules and RNA molecules, as well as analogs of DNA or RNA containing non-natural nucleotide analogs, non-native inter-nucleoside bonds, or both. The nucleic acid can be in any topological conformation.

The term "protein" or "polypeptide" as used herein indicates a polymeric form of amino acids composed of two or more amino acidic monomers and/or analogs thereof. As used herein, the term "amino acid" or "amino acidic monomer" refers to any natural and/or synthetic amino acids.

The term "enzyme" as used herein refers to any substance that catalyzes or promotes one or more chemical or biochemical reactions, which usually includes enzymes totally or partially composed of a polypeptide, but can include enzymes composed of a different molecule including polynucleotides.

The term "Heterologous" or "exogenous" refers to molecules, specifically polynucleotides or polypeptides or enzymes that are not present naturally in the host or that is at altered expression levels when compared to natural expression levels. These are expressed independently at levels of expression higher, equal or lower than the level of expression in a native organism.

As used herein, nucleic acid construct, nucleic acid (e.g., a polynucleotide), polypeptide, or host cell is referred to as "recombinant" when it is non-naturally occurring, artificial or engineered. In some embodiments, recombinant constructs contain two or more naturally-occurring sequences that are linked together in a way that does not occur naturally. A recombinant cell contains a recombinant polynucleotide. For clarity, reference to a cell of a particular strain refers to a parental cell of the strain as well as progeny and genetically modified derivatives of the same.

As used herein, "vector" refers to a nucleic acid molecule capable of transporting another nucleic acid to which it has been linked into a cell.

The terms "percent identity", "percent identical", "% identical" and "% identity" are used interchangeably herein to refer to the percent amino acid or polynucleotide sequence identity that is obtained by ClustalW2 analysis (EMBL—EBI, Cambridge, UK), counting the number of identical matches in the alignment and dividing such number of identical matches by the length of the reference sequence, and using the following ClustalW2 parameters to achieve slow/accurate pairwise optimal alignments—DNA/Protein Gap Open Penalty:15/10; DNA/Protein Gap Extension Penalty:6.66/0.1; Protein weight matrix: Gonnet series; DNA weight matrix: Identity; Toggle Slow/Fast pairwise alignments=SLOW or FULL Alignment; DNA/Protein Number of K-tuple matches:2/1; DNA/Protein number of best diagonals: 4/5; DNA/Protein Window size:4/5.

As used herein, the term "transformed" or "transformation" refers to the genetic alteration of a cell due to the uptake of non-native nucleic acid sequence through the cell membrane. The genetic material can be integrated into its genome or maintained as an episomal plasmid through multiple generations.

As used herein, the term "conjugated" or conjugation" refers to the transfer of genetic material between two cells through direct contact or by a temporary short connection. The transferred genetic material can be integrated into the genome or maintained as an episomal plasmid through multiple generations.

The terms "fold improvement" or "percent increase" as used herein refer to the increase in production levels in a recombinant strain relative to the production levels in the wildtype strain. For example, if the wildtype strain has a production of 5 mg/L and the recombinant strain has a production of 20 mg/L, the recombinant strain would have a 4 fold improvement in activity or a 300% improvement in activity relative to the wildtype strain.

The term "methanotrophs" or "methanotrophic bacteria" as used herein refers to bacteria that utilize methane as a source of carbon and energy. These bacteria are widely present in nature can be found in areas of high methane content such as oceans, mud, marshes, underground environments, soils, rice paddies and landfills. Some of these are obligate and can only use methane as a source of carbon and energy. Some of these are facultative and are known to additionally use other substrates such as succinate, acetate, pyruvate etc.

The terms "LDH" and "lactate dehydrogenase" are used interchangeably herein and used to refer to an enzyme having lactate dehydrogenase activity. An enzyme with lactate dehydrogenase activity catalyzes the conversion of pyruvate to lactate. The lactate dehydrogenase is a L-LDH or D-LDH if it catalyzes the conversion of pyruvate to L-lactate or pyruvate to D-lactate respectively.

The term "organic waste" herein refers to the components of waste that can be broken down into its base components in a reasonable amount of time by micro-organisms. Organic waste can be found in commonly occurring sources of waste such as municipal solid waste, green waste, food waste, paper waste, biodegradable waste, human waste, sewage, manure and slaughterhouse waste.

The term "Anaerobic digestion" as used herein refers to a set of processes wherein several types of microorganisms break down biodegradable material in the absence of oxygen. The end products are a gas comprising mostly methane and carbon dioxide, referred to as biogas, and a slurry or solid fraction, referred to as digestate. Different technologies are available for anaerobic digestion that vary in the process and process parameters affecting digestion.

The term "biogas" as used herein refers to the major product resulting from anaerobic digestion of waste. Typical composition of biogas is methane (50-75%), carbon dioxide (25-50%), nitrogen (0-10%), hydrogen (0-1%), hydrogen Sulphide (0-3%), oxygen (0-2%) and water vapour (3-5%). The biogas composition can vary depending on, among other factors, the type of waste, its organic matter load, feeding rate of digester and conditions of anaerobic digestion. Biogas is typically lighter than air and produces less calories by combustion compared to equal volume of natural gas. Biogas is typically used for heating, generating electricity or as cooking fuel.

The phrases "biogas cleaning" or "biogas upgrading" or "biogas scrubbing" as used herein refers to the process of removing the non-methane components of biogas. Depending on the use of the biogas, the extent of biogas cleaning can vary. Different methods of cleaning the various non-methane components of biogas are known and practiced. Hydrogen Sulphide can be removed by among others biological fixation by using iron oxidizing bacteria, dosing with iron chloride, water scrubbing, absorption activated carbon or bubbling through sodium hydroxide. Water vapor present in biogas can be removed by among others passive cooling, refrigeration, absorption into a drying medium, or adsorption into silica gel. Ammonia present in the biogas is usually in very low amounts and can be removed by water scrubbing. Oxygen and nitrogen are typically not present in large amounts in biogas and can be removed by adsorption with activated carbon, molecular sieves or membranes. "Biogas upgrading" more typically refers to the removal of carbon dioxide from the biogas to increase the energy content of the gas. Some technologies for removing carbon dioxide are commercially available and some are at the pilot or demo scale. Pressure swing adsorption is a process wherein the carbon dioxide can be removed by adsorption onto materials like activated carbon or zeolites under elevated pressure. Another method is removal of carbon dioxide by absorption. This is usually done by a counter current flow of biogas with a liquid in a column filled with plastic packaging. Absorption can be done using water, organic solvents or amine solutions. Another classical method used is membrane separation using materials that are permeable to carbon dioxide, water and ammonia.

The present invention discloses an eco-friendly way of handling the organic waste and producing commercially useful chemicals from the same by using recombinant methanotrophic bacteria.

The present invention provides recombinant methanotrophic bacteria capable of producing lactic acid from biogas or methane. The said recombinant methanotrophic bacteria include a heterologous nucleic acid or gene encoding for lactate dehydrogenase (ldh) enzyme.

The methanotrophs or methanotrophic bacteria are chosen for the present invention because they are unique in their ability to utilize methane as a sole carbon and energy source (Hanson, R. S., & Hanson, T. E., Methanotrophic bacteria. *Microbiological Reviews*, 60(2), pp 439-471 (1996)). However, methanotrophs are not well established industrial hosts. They are present in a wide variety of environments and play a critical role in the oxidation of methane in the natural world The methanotrophs are classified into two major groups based on the pathways used for assimilation of formaldehyde, the major source of cell carbon, and other physiological and morphological features. Type I methanotrophs employ the RuMP pathway for formaldehyde assimilation, whereas type II methanotrophs employ the serine pathway for formaldehyde assimilation. The use of enzymes known as methane monooxygenases—MMOs (EC 1.14.13.25)—to catalyze the oxidation of methane to methanol is a defining characteristic of methanotrophs. The oxidation of methane by aerobic methanotrophs is initiated by MMOs utilizing two reducing equivalents to split the O—O bonds of dioxygen. One of the oxygen atoms is reduced to form $H_2O$, and the other is incorporated into methane to form $CH_3OH$ (methanol). Two forms of MMOs have been found in methanotrophic bacteria, a soluble form (sMMO) and a membrane bound form, pMMO. Methanol is oxidized to formaldehyde by methanol dehydrogenase (MDH), an enzyme that's highly expressed in most methanotrophs. The further oxidation of formaldehyde to carbon dioxide via formate provides most of the reducing power required for the oxidation of methane. Multiple enzymes are known that catalyze the oxidation of formaldehyde to formate. The further oxidation of formate to carbon dioxide is catalyzed by an NAD-dependent formate dehydrogenase. Formaldehyde, produced from the oxidation of methane and methanol by methanotrophic bacteria, is assimilated to form intermediates of the central metabolic routes that are subsequently used for biosynthesis of cell material. The two known pathways used by methanotrophic bacteria for the synthesis of multicarbon compounds from formaldehyde are the serine pathway, in which 2 mol of formaldehyde and 1 mol of carbon dioxide are utilized to form a three-carbon intermediate, and the RuMP cycle for the assimilation of 3 mol of formaldehyde to form a three-carbon intermediate of central metabolism.

In one of the embodiments, the recombinant microorganism of the present invention is selected from a group of organisms comprising: Methylococcus capsulatus, Methylobacterium extorquens, Methylomicrobium album, Methylocapsa acidiphila, Methylobacterium organophilum, Methylobacterium mesophilicum, Methylobacterium dichloromethanicum, Methylocella silvestris, Methylosinus trichosporium, Methylobacillus flagellatus KT, Methylibium petroleiphilum PM1, Methylobacterium nodulans, Methylobacterium populi, Methylobacterium chloromethanicum, Methylacidiphilum infernorum V4, Methylophilus methylotrophus, Methylomonas methanica, Methylobacterium rhodesianum MB 126, Methylobacter tundripaludum, Methylobacterium sp. 4-46, Methylovorus glucosetrophus SIP3-4, Mycobacterium smegmatis, Methylobacterium rhodesianum, Methylosinus sporium, Methylocella palustris, Methylobacterium fujisawaense, Methylocystis parvus, Methylovulum miyakonense, Methylobacterium rhodinum, Methylocystis echinoides, Methylomonas rubra, Methylococcus thermophilus, Methylobacterium aminovorans, Methylobacterium thiocyanatum, Methylobacterium zatmanii, Acidithiobacillus ferrivorans, Methylobacterium aquaticum, Methylobacterium suomiense, Methylobacterium adhaesivum, Methylobacterium podarium, Methylobacter whittenburyi, Crenothrix polyspora, Clonothrix fusca, Methylobacter bovis, Methylomonas aurantiaca, Methylomonas fodinarum, Methylobacterium variabile, Methylocystis minimus, Methylobacter vinelandii, Methylobacterium hispanicum, Methylomicrobium japanense, Methylococcaceae bacterium, Methylosinus trichosporium Ob3b, and Methylocystis methanolicus.

Some species of the methanotrophs including, but not limited to, Methylococcus capsulatus, Methylocella silvestris, Methylobacterium extorquens, Methylosinus trichosporium etc. are well-characterized and basic molecular biology tools for host manipulation have been developed (http://www.methanotroph.org/wiki/genetics/).

In one embodiment, the recombinant methanotrophic bacteria for producing lactic acid is created from the Methylococcus capsulatus.

In an exemplary embodiment the recombinant methanotrophic bacteria for producing lactic acid is created from the Methylococcus capsulatus (Bath).

The recombinant methanotrophic bacteria comprise of methane oxidation pathway, pentose phosphate pathway, Entner-Duodoroff pathway, pathways for assimilation (serine and/or RuMP) and an exogenic nucleic acid encoding for lactate dehydrogenase enzyme. As a result, the provided recombinant methanotrophs are imparted with the capability to convert methane to lactic acid at levels significantly higher than that produced in the wildtype strain.

Expression of the heterologous genes may be accomplished by conventional molecular biology means (Green, M. R.; Sambrook, J (2001). *Molecular cloning: a laboratory manual*. Cold Spring Harbor, N.Y.: Cold Spring Harbor Laboratory). For example, the heterologous genes can be under the control of an inducible promoter or a constitutive promoter. The heterologous genes may either be integrated into a chromosome of the host microorganism, or exist as an extra-chromosomal genetic elements that can be stably passed on ("inherited") to daughter cells. Such extra-chromosomal genetic elements (such as plasmids, BAC, YAC, etc.) may additionally contain selection markers that ensure the presence of such genetic elements in daughter cells.

The heterologous nucleic acid or gene encoding for lactate dehydrogenase is from a micro-organism selected from a group consisting of E. coli, Pseudomonas aeruginosa and Pectobacterium carotovorum. Table 1 enlists the SEQ ID Nos. of the gene and polypeptide coding for ldh and micro-organisms/hosts from where it was taken.

TABLE 1

| SEQ ID | Gene | Host |
| --- | --- | --- |
| SEQ ID 1 | Lactate dehydrogenase - DNA | E. coli |
| SEQ ID 2 | Lactate dehydrogenase - Amino acid | E. coli |
| SEQ ID 3 | Lactate dehydrogenase - DNA | P. aeruginosa |
| SEQ ID 4 | Lactate dehydrogenase - Amino acid | P. aeruginosa |
| SEQ ID 5 | Lactate dehydrogenase - DNA | P. carotovorum |
| SEQ ID 6 | Lactate dehydrogenase - Amino acid | P. carotovorum |

In one embodiment of the present invention, the heterologous nucleic acid or gene encoding for lactate dehydrogenase enzyme, included in the recombinant methanotrophic bacterium, is selected from sequences set forth as SEQ ID NO.1, 3, 5, or a combination thereof.

In an exemplary embodiment of the present invention, the heterologous nucleic acid or gene encoding for lactate dehydrogenase enzyme, included in the recombinant methanotrophic bacterium, is a Lactate dehydrogenase gene (SEQ ID NO. 1) taken from E. coli. The heterologous nucleic acid or gene encodes an amino acid sequence that is at least 80% identical to a reference amino acid of Escherichia coli.

The heterologous nucleic acid or gene encoding for the lactate dehydrogenase enzyme set forth as SEQ ID NO.1, 3, and 5 has a corresponding amino acid sequence set forth as SEQ ID No: 2, 4, and 6.

The heterologous nucleic acid encoding for the lactate dehydrogenase enzyme comprises an amino acid sequence that is at least 80% identical to a reference amino acid sequence selected from a group consisting of SEQ ID Nos: 2, 4 and 6.

The lactic acid is chiral and has two optical isomers. One is known as L(+)-lactic acid or (S)-lactic acid and the other, its mirror image, is D(−)-lactic acid or (R)-lactic acid. For the production of D and L forms of Lactic acid, the enzymes involved are D-lactate dehydrogenase (D-LDH) and L-lactate dehydrogenase (L-LDH), respectively.

In one of the embodiments, lactate dehydrogenase enzyme included in the recombinant methanotrophic bacteria is D-lactate dehydrogenase or L-lactate dehydrogenase. As a result of that the lactic acid produced by the recombinant methanotrophic bacteria is either D-Lactic acid or L-lactic acid depending on whether the gene encoding for the D-lactate dehydrogenase or L-lactate dehydrogenase is included.

In one of the embodiments, the recombinant methanotrophic bacteria are engineered to produce D-lactic acid.

In an alternate embodiment, the recombinant methanotrophic bacteria are engineered to produce L-lactic acid.

The present invention also provides for improving the production of lactic acid above basal levels achieved in the recombinant methanotrophic bacteria. In one embodiment the lactic acid production in recombinant methanotrophic bacteria with heterologous lactate dehydrogenase is at least 5 fold higher than the wildtype methanotroph. In an exemplary embodiment, the lactic acid production in recombinant methanotrophic bacteria with heterologous lactate dehydrogenase having a gene sequence set forth as SEQ ID NO.2 is at least 10 fold higher than the wildtype methanotroph. In another exemplary embodiment, the lactic acid production in the recombinant methanotrophic bacteria with heterologous lactate dehydrogenase having a gene sequence set forth as SEQ ID NO.1 is at least 20 fold higher than the wildtype methanotroph.

In one of the embodiments, improvement in production of lactic acid above basal levels is achieved in the recombinant methanotrophic bacteria capable of converting biogas or methane to lactic acid by overexpressing or/and down-regulating or/and deleting genes coding for key enzymes. The basal levels indicate amount of lactic acid produced by the recombinant methanotrophic bacteria when fed with biogas or methane. In some embodiments the lactic acid is at least 5 fold higher than that in the wildtype strain. In other embodiments it is at least 10, 15 or 20 fold higher than the wildtype methanotroph strain.

As used herein, the term "overexpress" is intended to encompass increasing the expression or activity of a gene or protein to a level greater than the cell normally produces. It is intended that the term encompass-overexpression of endogenous, as well as heterologous gene or proteins. Overexpression of genes or proteins can be done by conventional molecular biology methods. In some embodiments, the genes can be overexpressed by introducing additional copies of the genes on the chromosome or extra-chromosomally on plasmids, BACs or YACs. In certain embodiments the expression can be increased by optimizing the nucleotide sequence for expression in the specific host such as through codon optimization. In other embodiments, the gene expression can be increased by altering the promoter or ribosome binding site operably linked to the gene. In yet other embodiments the gene activity can be increased through mutations in the gene that enhance the enzymatic activity.

The term "down-regulated" or "deleted" used herein with reference to a gene or protein, indicates any modification in the genome and/or proteome of a microorganism that eliminates or reduces the biological activity of the gene, protein or enzyme either directly or indirectly. For example, deletion or downregulation of gene or protein can be performed by deleting or mutating a native or heterologous polynucleotide encoding for the gene or protein in the microorganism, by deleting or mutating a native or heterologous polynucleotide encoding for an enzyme involved in the pathway for the synthesis of the gene or protein in the microorganism, by activating a further native or heterologous molecule that inhibits the expression of the gene or protein in the microorganism. In particular, in some embodiments inactivation of a gene or protein such as an enzyme can be performed by deleting from the genome of the recombinant microorganism one or more endogenous genes encoding for the enzyme.

For assembly of the constructs to enable overexpression or downregulation or deletion of specific gene, conventional molecular biology methods can be used (Green, M. R.; Sambrook, J (2001). *Molecular cloning: a laboratory manual*. Cold Spring Harbor, N.Y.: Cold Spring Harbor Laboratory; Ellis, T., Adie, T., & Baldwin, G. S. (2011), DNA assembly for synthetic biology: from parts to pathways and beyond. *Integrative Biology: Quantitative Biosciences from Nano to Macro*, 3(2), 109-18). Assembly of DNA parts through restriction digestion and ligation is well-established and known to those skilled in the art (Green, M. R.; Sambrook, J (2001). *Molecular cloning: a laboratory manual*. Cold Spring Harbor, N.Y.: Cold Spring Harbor Laboratory). Other methods that offer standardized, scarless, sequence independent, multi piece DNA assembly such as SLIC (Sequence and Ligation Independent Cloning), Gibson assembly, CPEC (Circular Polymerase Extension Cloning) or SLiCE (Sequence and Ligation Cloning Extract) have more recently been established (https://j5.jbei.org/j5manual/pages/22.html). In some embodiments, SLIC based assembly is used for generating DNA constructs or vectors for overexpression or downregulation or deletion. In other embodiments CPEC is used for assembly of DNA constructs for overexpression, deletion or down-regulation. In further embodiments, methods such as site-directed mutagenesis, transposon mutagenesis, Crispr/Cas assisted genome engineering and recombineering can be used directly for overexpression, down-regulation or deletion of specific gene or protein.

In one embodiment, additional improvement in production of lactic acid above basal levels is achieved in the recombinant methanotrophic bacteria capable of converting biogas or methane to lactic acid by overexpressing genes encoding for enzymes which are selected from a group consisting of glyceraldehyde 3-phosphate dehydrogenase (SEQ ID Nos. 23, 24), glucose-6-phosphate isomerase (SEQ ID Nos. 11, 12), 2,3-bisphosphoglycerate-independent phosphoglycerate mutase (SEQ ID Nos. 17, 18), glycerate 2-kinase (SEQ ID Nos.19, 20), hexulose-6-phosphate synthase (SEQ ID Nos.7, 8), Transaldolase (SEQ ID Nos.13, 14), phosphor fructo kinase (SEQ ID Nos.9, 10), 2,3-bisphosphoglycerate-dependent phosphoglycerate mutase (SEQ ID Nos.15, 16), enolase (SEQ ID Nos.21, 22), ribulose phosphate 3-epimerase (SEQ ID Nos.25, 26) and methanol dehydrogenase (SEQ ID Nos.27, 28, 29, 30) or any combination thereof. Table 2 enlists the over-expressed genes, their SEQ ID Nos. and host organisms.

TABLE 2

| SEQ ID | Gene | Host |
|---|---|---|
| SEQ ID 7 | Hexulose 6-phosphate synthase - DNA | *M. capsulatus* |
| SEQ ID 8 | Hexulose 6-phosphate synthase - Amino acid | *M. capsulatus* |
| SEQ ID 9 | Phospho fructo kinase - DNA | *M. capsulatus* |
| SEQ ID 10 | Phospho fructo kinase - Amino acid | *M. capsulatus* |
| SEQ ID 11 | Glucose-6-phosphate isomerase - DNA | *M. capsulatus* |
| SEQ ID 12 | Glucose-6-phosphate isomerase - Amino acid | *M. capsulatus* |
| SEQ ID 13 | Transaldolase - DNA | *M. capsulatus* |
| SEQ ID 14 | Transaldolase - Amino acid | *M. capsulatus* |
| SEQ ID 15 | 2,3-bisphosphoglycerate-dependent phosphoglycerate mutase - DNA | *E. coli* |
| SEQ ID 16 | 2,3-bisphosphoglycerate-dependent phosphoglycerate mutase - Amino acid | *E. coli* |
| SEQ ID 17 | 2,3-bisphosphoglycerate-independent phosphoglycerate mutase - DNA | *E. coli* |
| SEQ ID 18 | 2,3-bisphosphoglycerate-independent phosphoglycerate mutase - Amino acid | *E. coli* |
| SEQ ID 19 | Glycerate 2-kinase - DNA | *E. coli* |
| SEQ ID 20 | Glycerate 2-kinase - Amino acid | *E. coli* |

TABLE 2-continued

| SEQ ID | Gene | Host |
| --- | --- | --- |
| SEQ ID 21 | Enolase - DNA | M. capsulatus |
| SEQ ID 22 | Enolase - Amino acid | M. capsulatus |
| SEQ ID 23 | Glyceraldehye 3-phosphate dehydrogenase - DNA | M. capsulatus |
| SEQ ID 24 | Glyceraldehye 3-phosphate dehydrogenase - Amino acid | M. capsulatus |
| SEQ ID 25 | Ribulose phosphate 3-epimerase - DNA | M. capsulatus |
| SEQ ID 26 | Ribulose phosphate 3-epimerase - Amino acid | M. capsulatus |
| SEQ ID 27 | Methanol dehydrogenase larger subunit - DNA | M. capsulatus |
| SEQ ID 28 | Methanol dehydrogenase larger subunit - Amino acid | M. capsulatus |
| SEQ ID 29 | Methanol dehydrogenase smaller subunit - DNA | M. capsulatus |
| SEQ ID 30 | Methanol dehydrogenase smaller subunit - Amino acid | M. capsulatus |

In one embodiment, additional improvement in production of lactic acid above basal levels is achieved in the recombinant methanotrophic bacteria capable of converting biogas or methane to lactic acid by down-regulating one or more genes encoding for enzymes which are selected from a group consisting of acetate kinase, acetate synthase, succinyl CoA synthetase, and malate dehydrogenase or any combination thereof.

The present invention further provides for a method of creating the said recombinant methanotrophic bacteria for producing lactic acid. The recombinant methanotrophic bacteria are selected from the group of methanotrophs as detailed in the earlier part of the specification.

In one of the embodiments, the recombinant methanotrophic bacteria for producing lactic acid is created from the *Methylococcus capsulatus* (Bath). The gene encoding for lactate dehydrogenase enzyme, which catalyzes the conversion of pyruvate to lactate, is conjugated into *M. capsulatus*. In the process, the gene encoding for lactate dehydrogenase enzyme from a suitable host is amplified from genomic DNA using primers flanked with one or more restriction enzymes. Alternately, the gene is synthesized together with flanking sequences for one or more restriction enzymes. The said gene is restriction digested and ligated into a cloning vector to create a first construct for purpose of gene sequence verification, if the gene is amplified from genomic DNA. The said gene is restriction digested and ligated with a broad host range vector to create a second construct for expression in the *M. capsulatus*. The first construct containing the heterologous lactate dehydrogenase gene is transformed into *E. coli* BL21 competent cells by chemical transformation. The transformants, from previous step, are selected so as to verify activity of the lactate dehydrogenase. The second construct is conjugated into the *M. capsulatus* (Bath) to obtain the recombinant *M. capsulatus*.

In one specific embodiment, lactate dehydrogenase gene (Genbank U36928.1; P52643; SEQ ID No. 1) from *E. coli* was amplified from genomic DNA using primers flanked with BamH1 and HindIII restriction enzymes. The amplified gene was restriction digested and cloned into BamHI and HindIII sites in the pET21a (Novagen Cat No: 69740-3CN) vector to create pSB101. The gene was then sequence verified. The cloned gene was re-amplified with primers with Sac1 and SphI overhangs. The amplified gene was restriction digested with SacI and SphI and cloned into the SacI/SpHI sites in the broad host range vector pMHA201 (from Prof. Colin Murrell, University of Norwich), downstream of sigma 70 promoter, to create pSB102. pMHA201 (See Ali and Murrell 2009,) is a plasmid with a broad range Origin of replication (OriV), Kanamycin resistance gene, Ampicillin resistance gene and OriT for conjugative transfer. Plasmid pSB102 was sequence verified.

Methanotroph strains were cultivated in nitrate mineral salt (NMS) medium (http://www.methanotroph.org/wiki/culturing-tips/). NMS agar plates were prepared with 1.5% (w/v) Bacto agar. Antibiotics were added as required: Kanamycin (30 µg/ml) and Gentamicin (5 µg/ml). Methanotrophs were typically grown in 250 ml conical flasks with 24/29 joint containing 50 ml NMS medium. Flasks were sealed with suba-seals and gassed with 50 ml (i.e. ~20%) methane/carbon dioxide (95/5, v/v mix). Methanotrophs grown on NMS agar plates were incubated in gas-tight container under a methane/air/carbon dioxide atmosphere (50/45/5, by vol.) at the appropriate temperature. The gas was replenished every 2 days until colonies formed, usually within 5-10 days. *M. capsulatus* (from Prof. Colin Murrell, University of Norwich) derived strains were incubated at 45° C. Conjugation of pSB102 into *M. capsulatus* was done based on the protocol described by Martin, H., & Murrell, J. C. (1995). Methane monooxygenase mutants of *Methylosinus trichosporium* constructed by marker-exchange mutagenesis. *FEMS Microbiology Letters*, 127(3), pp 243-248. 30 mL of *M. capsulatus* culture was spun down and resuspended in 5 mL of NMS media. 2 mL of *E. coli* S.17 lambda pir bearing the plasmid to be conjugated was spun down, washed with 1 mL of NMS and resuspended again in 1 mL of NMS. The two cultures were mixed and filtered onto a 0.2µ nitrocellulose membrane. The membrane was placed on an NMS agar plate containing 0.02% (w/v) proteose peptone and incubated for a duration of 24 hours at 37° C. in a gas-tight container under a methane/air/carbon dioxide atmosphere (50/45/5, by vol.). Following incubation, the cells were washed with 1 ml NMS and collected by centrifugation (7,000×g for 5 minutes). Aliquots (50-100 µl) of the cells were spread onto NMS plates containing 30 µg/ml kanamycin for plasmid selection and incubated at 45° C. in a gas-tight container under a methane/air/carbon dioxide atmosphere (50/45/5, by vol.). Colonies typically formed on the plates after 8-12 days. Colonies were re-streaked onto NMS agar plates with 30 ug/ml of kanamycin to confirm the true recombinant strains.

The present invention also provides a process of organic waste management by using the recombinant methanotrophic bacteria. The process broadly involves (a) converting the waste to biogas by anaerobic digestion, (b) converting biogas to lactic acid by using the recombinant microorganisms, or alternatively scrubbing the biogas so produced to have methane and then converting it to lactic acid by using the recombinant microorganisms.

In one embodiment, biogas is used as an input for producing lactic acid by employing the recombinant methanotrophic bacteria. The method includes:

A. Anaerobically digesting organic waste to break it down to biogas via three distinct stages of hydrolysis, acetogenesis, and methanogenesis. In the first stage, a group of microorganisms comprising fermentative bacteria, secreting enzymes (lipases, proteases, cellulases, amylases, etc.), hydrolyses polymeric materials to monomers such as sugars and amino acids. In the next stage, products of the first stage are subsequently converted by a second group of bacteria comprising acetogenic bacteria to simple organic acids, carbon dioxide and hydrogen. In the final stage, a third group of bacteria comprising methanogens converts carbon dioxide, hydrogen and acetate to methane. Various aspects of the process of breaking down of solid waste have been well-researched, stream lined, and solutions at various scales have been developed. The most valuable component of biogas is methane ($CH_4$) which constitutes around 50-75%, the remaining portion comprises carbon dioxide ($CO_2$) and small percentages of other gases. The overall process of anaerobic digestion and output varies depending on the size of plant, type of waste, process conditions for fermentation, type of fermentation process etc.

B. Cleaning up the biogas to remove carbon dioxide and other impurities present in the gas. The cleaning further includes two steps—(i) cleaning of hydrogen sulphide ($H_2S$), $NH_3$, water vapour and other impurities, and (ii) removal of carbon dioxide. Methods employed for biogas purification include, but not limited to, chemical absorption, high pressure water scrubbing, pressure swing adsorption, cryogenic separation, and membrane separation. The steps employed are well-researched and optimised to achieve efficient purification. The main output from this process is the methane gas.

C. Third step of the method plays most significant part where the methane gas is converted to lactic acid by using the recombinant methanotrophic bacteria capable of metabolising methane to produce lactic acid (nonnative). The process of converting methane to lactic acid includes:
  (1) Conversion of methane to methanol involves oxidation of methane to methanol by the methane monooxygenase enzyme (EC number EC 1.14.13.25). As mentioned above the methane monooxygenases (MMOs) are unique enzymes that can catalyze the oxidation of methane in the presence of oxygen.
  (2) Conversion of methanol to formaldehyde involves oxidation of methanol to formaldehyde by methanol dehydrogenase (EC 1.1.1.244). Gram negative methanotrophs have a periplasmic methanotroph that is cytochrome c dependent. Gram positive methanotrophs have a NAD dependent enzyme that catalyzes this step.
  (3) Conversion of formaldehyde to pyruvate via central carbon metabolism involving assimilation of formaldehyde into central carbon metabolism of the methanotrophs and conversion to pyruvate via the steps of the RuMP pathway or serine pathway. Formaldehyde is a key intermediate that gets assimilated into the central carbon metabolism.
  4) Conversion of pyruvate to lactate by lactate dehydrogenase (EC 1.1.1.27/EC 1.1.1.28)—one of the key intermediates on central carbon metabolism is pyruvate, a hydroxy acid. Lactate dehydrogenase enzyme is not native to methanotrophs. Heterologous expression of lactate dehydrogenase is required for the conversion to lactate.
  5) Separating and collecting the lactic acid so produced by the recombinant methanotrophic bacteria Suitable conditions for conversion of methane or biogas to lactic acid depend on the temperature optimum, pH optimum, and nutrient requirements of the host microorganism and are known by those skilled in the art. These culture conditions may be controlled by methods known by those skilled in the art. For example, *M. capsulatus* are typically grown at temperatures of about 37° C. to about 50° C. and a pH of about pH 3.0 to pH 7.0. Growth media used for *M. capsulatus* typically include nitrate mineral salts, ammonium mineral salts and other relevant minimal media that usually do not contain other sources of carbon. The temperature maintained throughout the step C where the methane gas is converted to lactic acid by using the recombinant methanotrophic bacteria is in the range of 37 to 50° C. However, best results are obtained when the temperature maintained throughout the step C is 45° C. Further, the maintained pH is maintained throughout the step C in the range of about 3 to 7. However, the best results are obtained where the pH is maintained within the range of 4-6. A dissolved oxygen concentration of <20% is preferably maintained throughout the step C.

In an alternate embodiment, biogas is directly used as input without cleaning up the biogas to remove carbon dioxide and other impurities, hence omitting the step B provided for the above described embodiment, for producing lactic acid by employing the recombinant microorganisms. Depending on the type of substrates used, anaerobic digestion, biogas cleaning etc. the ratio of methane to carbon dioxide in the input may vary. In some embodiments the ratio of methane to carbon dioxide is 95%:5%. In other embodiments it can be 50% methane:50% carbon dioxide. In another alternate embodiment, the biogas used as the input has varying ratios of methane to carbon dioxide such as, but not limited to, from 95% methane:5% $CO_2$ to 50% methane:50% $CO_2$.

In another embodiment, methane gas is used as an input for producing lactic acid by employing the recombinant methanotrophic bacteria. The process of converting methane to lactic acid includes:
  (1) Conversion of methane to methanol involves oxidation of methane to methanol by the methane monooxygenase enzyme (EC number EC 1.14.13.25). As mentioned above the methane monooxygenases (MMOs) are unique enzymes that can catalyze the oxidation of methane in the presence of oxygen.
  (2) Conversion of methanol to formaldehyde involves oxidation of methanol to formaldehyde by methanol dehydrogenase (EC 1.1.1.244). Gram negative methanotrophs have a periplasmic methanotroph that is cytochrome c dependent. Gram positive methanotrophs have a NAD dependent enzyme that catalyzes this step.
  (3) Conversion of formaldehyde to pyruvate via central carbon metabolism involving assimilation of formaldehyde into central carbon metabolism of the methanotrophs and conversion to pyruvate via the steps of the RuMP pathway or serine pathway. Formaldehyde is a key intermediate that gets assimilated into the central carbon metabolism.
  4) Conversion of pyruvate to lactate by lactate dehydrogenase (EC 1.1.1.27/EC 1.1.1.28)—one of the key intermediates on central carbon metabolism is pyruvate, a hydroxy acid. Lactate dehydrogenase enzyme is not native to methanotrophs. Heterologous expression of lactate dehydrogenase is required for the conversion to lactate.
  5) Separating and collecting the lactic acid so produced by the recombinant methanotrophic bacteria.

The temperature maintained throughout the process is in the range of 37 to 50° C. However, best results are obtained when the temperature maintained throughout the process is 45° C. Further, the maintained pH is maintained throughout is in the range of about 3 to 7. However, the best results are obtained where the pH is maintained within the range of 4-6. A dissolved oxygen concentration of <20% is preferably maintained throughout.

The lactic acid finds its use in various industries and commercially useful products. The L-Lactic acid is added into foods and beverages when a tart, acid taste is desired, and is commonly used as a non-volatile acidulant. Both D- and L-lactic acid are used as raw materials in the production of compounds such as polylactides and biodegradable polymers/plastics, and applications also exist for these acids in cosmetics and pharmaceuticals.

The present invention provides a cradle to cradle environment-friendly and commercially viable solution for managing organic waste. The target chemical lactic acid, produced from the organic waste by employing the recombinant microbes, is an excellent building block for manufacturing variety of commercially viable products including, but not limited to, biodegradable plastics. Poly Lactic Acid (PLA), biodegradable polymer of lactic acid, is a linear aliphatic polyester produced by poly-condensation of naturally produced lactic acid or by the catalytic ring opening of the lactide group. The PLA could be an alternative to the conventional plastic materials. The PLA being biodegradable can be disposed in safe and ecologically sound manner, through disposal processes (waste management) like composting, soil application, and biological wastewater treatment. The by-products of the biodegradation process of compostable polymers have very minimal environmental effects and are primarily water, $CO_2$, and biomass similar to plant biomass. High production cost of the biodegradable polymers as compared to conventional plastics has been an inhibiting factor for extensive use of biodegradable polymers. It is of utmost importance, keeping environmental sustainability in mind, to implement immediate use for biodegradable plastics in several areas such as industrial packaging, wrapping, milk sachets, foodservice, personal care, pharmaceuticals, surgical implants, medical devices, recreation, etc. The present invention brings down the overall cost of lactic acid production by using waste materials and hence production cost of PLA. The increase in production and use of cheaper biodegradable plastic will effectively reduce the disposability problem associated with the use of conventional plastics broadly in two ways firstly, the waste biodegradable plastics do not create environmental hazard and can be converted to target chemicals which may be used again to produce useful products, and secondly, this also solves the problem of segregating non-biodegradable and biodegradable materials in the waste stream of Municipal Solid Waste (MSW).

EXAMPLES

The present invention is explained further in the following specific examples which are only by way of illustration and are not to be construed as limiting the scope of the invention.

Example 1: Cloning Lactate Dehydrogenase into a Bacterial Vector

Lactate dehydrogenase gene (Genbank U36928.1; P52643; SEQ ID No. 1) from *E. coli* was amplified from genomic DNA using primers flanked with BamH1 and HindIII restriction enzymes. The amplified gene was restriction digested and cloned into BamHI and HindIII sites in the pET21a (Novagen Cat No: 69740-3CN) vector to create pSB101. The gene was then sequence verified.

Figure 1:
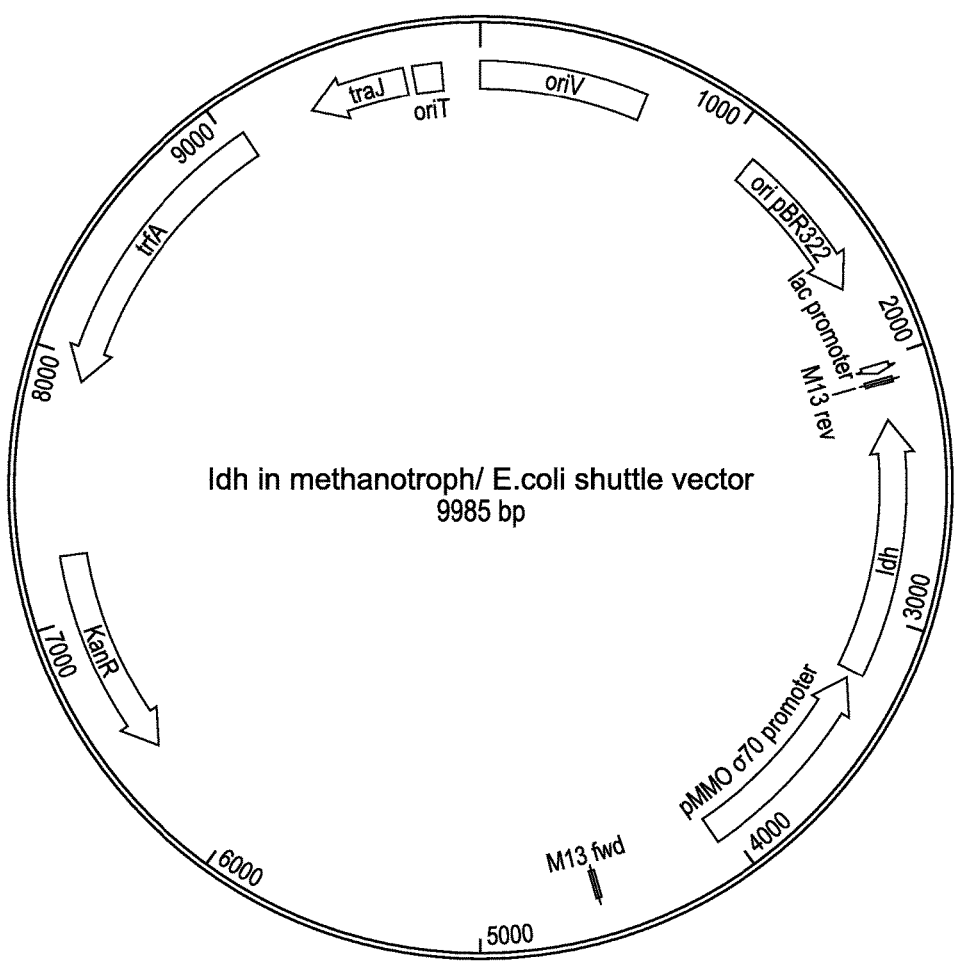
FIG. 1 illustrates a Lactate dehydrogenase gene (ldh) cloned in an E. coli/Methanotroph shuttle vector under the sigma 70 promoter, according to one embodiment.

The cloned gene was re-amplified with primers with SacI and SphI overhangs. The amplified gene was restriction digested with SacI and SphI and cloned into the SacI/SphHI sites in the broad host range vector pMHA201 (From Prof. Colin Murrell, University of Norwich), downstream of sigma 70 promoter, to create pSB102. pMHA201 (Alit, H., & Murrell, J. C., *Development and validation of promoter-probe vectors for the study of methane monooxygenase gene expression in Methylococcus capsulatus Bath.*, Microbiology, 155(3), pp 761-771 (2009); doi:10.1099/mic.0.021816-0) is a plasmid with a broad range Origin of replication (OriV), Kanamycin resistance gene, Ampicillin resistance gene and OriT for conjugative transfer. Plasmid pSB102 (FIG. 1) was sequence verified.

Example 2: Verification of Activity of Lactate Dehydrogenase

Vector pSB101 was transformed into *E. coli*. BL21 competent cells (NEB, Cat. Num: 2530H) by chemical transformation. True transformants were selected by plating cells on LB agar plates containing 50 ug/ml of kanamycin.

Single colonies of the true transformants were used to inoculate 5 ml of LB media containing 50 ug/ml of kanamycin in 50 ml culture tubes. The cultures were incubated for a duration of 16 hours at 37° C. at 200 rpm. The cultures were used to inoculate 25 ml LB media containing 50 ug/ml of kanamycin in 100 ml flasks at a ratio of 1:1000. The cultures were incubated at 37° C. at 200 rpm. The culture was induced with 0.1 mM IPTG at an OD of 0.8. Samples were taken from the flasks at different time intervals (up to 24 hours) for lactic acid analysis. The samples were centrifuged at 10,000 rpm for 20 mins to separate the cells from the supernatant. The supernatant was analyzed for lactic acid levels.

Figure 2:
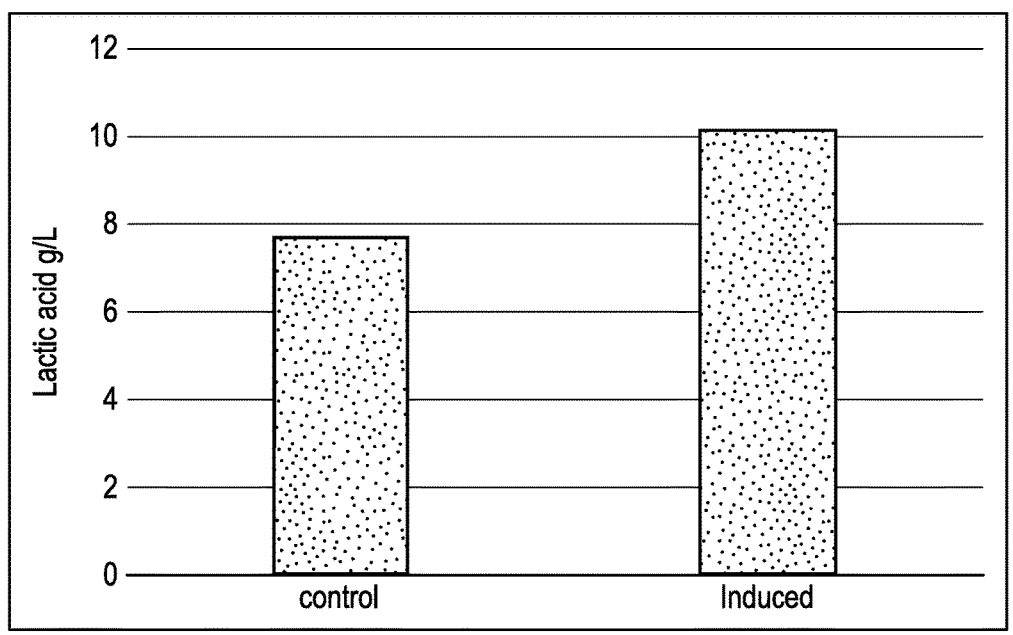
FIG. 2 is a graph illustrating the comparison between induced culture and un-induced control, where the induced cultures with Lactate gene overexpressed from pSB101 tested for activity in E. coli shows higher lactate levels (>20% higher) when compared to un-induced control.

Lactic acid was estimated by HPLC. Samples were run on a C18 column using 25 mM phosphate buffer pH 2.8 and Acetonitrile at 95%:5% at 0.5 ml/min. Lactic acid amounts was measured at 210 nm using standards. Induced samples showed at least 20% higher amount of lactic acid compared to un-induced control samples (FIG. 2).

Example 3: Conjugation of pSB102 into Methanotroph Strains

Methanotroph strains were cultivated in nitrate mineral salt (NMS) medium. NMS medium was prepared following the protocol outlined at http://www.methanotroph.org/wiki/culturing-tips and included here. NMS agar plates were prepared with 1.5% (w/v) Bacto agar. Antibiotics were added as required: Kanamycin (30 µg/ml) and Gentamicin (5 µg/ml).

Methanotrophs were typically grown in 250 ml conical flasks with 24/29 joint containing 50 ml NMS medium. Flasks were sealed with suba-seals (Sigma Aldrich, Cat Num: Z279773-10EA) and gassed with 50 ml (i.e. ~20%) methane/carbon dioxide (95/5, v/v mix). *M. capsulatus* (From Prof. Colin Murrell, University of Norwich) derived strains were incubated at 45° C. with shaking at 200 rpm. *M. trichosporium* (From Prof. Colin Murrell, University of Norwich) derived strains were incubated at 30° C. A typical methanotrophic culture took about 4-6 days to reach stationary phase. Methanotrophs grown on NMS agar plates were incubated in gas-tight container under a methane/air/carbon dioxide atmosphere (50/45/5, by vol.) at the appropriate temperature. The gas was replenished every 2 days until colonies formed, usually within 5-10 days depending on the strain.

Conjugation of pSB102 into *M. capsulatus* was done based on the protocol described by Martin, H., & Murrell, J. C., Methane monooxygenase mutants of *Methylosinus trichosporium* constructed by marker-exchange (1995). 30 mL of methanotroph culture was spun down and resuspended in 5 mL of NMS media. 2 mL of *E. coli* S.17 lambda pir bearing the plasmid to be conjugated was spun down, washed with 1 mL of NMS and resuspended again in 1 mL of NMS. The two cultures were mixed and filtered onto a 0.2μ nitrocellulose membrane. The membrane was placed on an NMS agar plate containing 0.02% (w/v) proteose peptone and incubated for a duration of 24 hours at 37° C.

Following incubation, the cells were washed with 1 ml NMS and collected by centrifugation (7,000×g for 5 minutes). Aliquots (50-100 μl) of the cells were spread onto NMS plates containing 30 μg/ml kanamycin for plasmid selection and incubated at 45° C. in a gas-tight container under a methane/air/carbon dioxide atmosphere (50/45/5, by vol.). Colonies typically formed on the plates after 8-12 days. Colonies were re-streaked onto NMS agar plates with 30 ug/ml of kanamycin to confirm the true transformants.

Example 4: Growth and Assay of Methane to Lactic Acid Conversion

Positive transformants of *M. capsulatus* containing pSB102 were verified by PCR. These were inoculated into 5 ml of liquid NMS media taken in 30 ml culture tubes and sealed with suba seals. 15 ml of Methane mixture (95% CH4; 5% CO2) was introduced into the culture tube using a syringe. The tubes were incubated at 45° C. at 200 rpm agitation. Once the culture OD reached 1, the cultures was centrifuged and the supernatant samples were taken and assayed for lactic acid. D-lactic acid was assayed using a kit (Megazyme International, K-DATE kit) according to manufacturer's protocol. L-Lactic acid was assayed using a kit (Megazyme International, L-DATE kit) according to manufacturers' protocol. Methanotroph strains transformed with lactate dehydrogenase gene (STB1; SEQ ID 1) showed >20 fold higher levels of lactic acid compared to wildtype control (Control and STB1 in FIG. 3).

Example 5: Growth and Assay of Methane to Lactic Acid Conversion with Different Lactate Dehydrogenases and Varying Promoters Lactate dehydrogenase genes from *E. coli*, *P. aeruginosa* (MTCC 424) and *P. carotovorum* (MTCC 1428) were amplified from the respective genomes, cloned under the control of methanol dehydrogenase promoter (PmxaF) or sigma 70 promoter (σ70) (Alit, H., & Murrell, J. C., *Development and validation of promoter-probe vectors for the study of methane monooxygenase gene expression in Methylococcus capsulatus* Bath, Microbiology, 155(3), pp 761-771 (2009); doi:10.1099/mic.0.021816-0), and tested for methane to lactic acid conversion. To clone PmxaF promoter, the promoter was amplified from *M. capsulatus* and cloned into pMHA201 vector in place of the sigma 70 promoter using CPEC (Circular Polymerase Extension Cloning, See Quan and Tian 2009). Positive clones were verified by PCR.

Six constructs (*E. coli* ldhA under PmxaF and σ70 promoter; *P. aeroginosa* ldh under PmxaF and σ70 promoter and *P. carotovorum* ldh under PmxaF and σ70 promoter) were conjugated into *M. capsulatus* based on the protocol described by Martin & Murrell 1995. Positive transformants were selected on NMS plates with 30 μg/ml of Kanamycin.

Sequence verified clones were used to inoculate 5 ml of NMS media containing 30 μg/ml of Kanamycin taken in 30 ml culture tubes. The cultures tubes were sealed with suba seals. 15 ml of Methane mixture (95% CH$_4$; 5% CO$_2$) was introduced into the culture tube using a syringe. The tubes were incubated at 45° C. at 200 rpm agitation. Samples were taken at OD 1.0 and tested for lactic acid using Megazyme lactic acid assay kit according to manufacturer's protocol. FIG. 3 depicts the lactic acid production from the recombinant methanotroph strain with different heterologous lactate dehydrogenases. Recombinant methanotroph strains, except for STB6, had at least 5 fold higher lactic acid compared to control and as much as 20 fold higher lactic acid control when compared to control. Strains tested were Control—wildtype *M. capsulatus*; STB1/STB4—*M. capsulatus* with *E. coli* ldh cloned under sigma 70' and PmxaF; STB2/STB5—*M. capsulatus* with *P. aeruginosa* ldh under sigma 70 and PmxaF; STB3/STB6—*M. capsulatus* with *P. carotovorum* ldh under sigma 70 and PmxaF.

Example 6: Growth of Methanotroph Strains on Biogas Generated from Organic Waste Methanotroph strain *Methylococcus capsulatus* was grown on methane and biogas to test the effect of biogas constituents on growth.

Biogas used for this analysis was from an anaerobic digester that processes kitchen waste. Food waste was anaerobically digested using BioOrja biomethanation reactor (GPS Renewables, Bangalore). Bioorja generates 70 kg of LPG equivalent from 1 ton of food waste. The composition of the biogas was largely 60-65% CH$_4$; 35-30% CO$_2$; Traces—H$_2$S; Traces—NH$_3$. For comparative methane, a commercial mixture of 95% CH$_4$: 5% CO$_2$ was used. Nitrate mineral salts medium was used for strain growth. The methanotroph strain, *M. capsulatus*, was inoculated into 5 ml of NMS media taken in 30 ml culture tubes. The tubes were sealed with suba seals. 15 ml of methane or biogas was fed into the tubes using a syringe. The tubes were incubated at 45° C. at 200 rpm agitation. Samples were taken from the tubes every 24 hours and cell growth was measured by monitoring OD at 600 nm. When growth was compared for *M. capsulatus* between biogas and methane, the growth profile of the strain on biogas was similar to the growth profile on commercial methane mixture (FIG. 4).

Example 7: Growth and Assay of Biogas to Lactic Acid Fermentation

The recombinant *Methylococcus capsulatus* with heterologous lactate dehydrogenase gene (SEQ ID No.1, Strain STB 4) was grown in biogas generated from organic waste and tested for conversion of biogas to lactic acid.

Recombinant strain and control were inoculated in 5 ml of NMS media containing 30 ug/ml of Kanamycin taken in 30 ml culture tubes. The culture tubes were sealed with suba seals. 15 ml of biogas was fed into the culture tubes using a syringe. Biogas used for this analysis was obtained from kitchen waste digested using the BioOrja reactor. The composition of the biogas was largely 60-65% CH$_4$; 35-30% CO$_2$; Traces—H$_2$S; Traces—NH$_3$. The cells were grown in conditions optimal for growth—45° C. and 200 rpm. 0.1 ml samples were taken at every 24 hours and measured for OD (600 nm) and lactic acid levels. The samples were centrifuged and the supernatant was assayed for lactic acid using the Megazyme lactic acid kit according to manufacturer's protocol. Lactic acid levels in the recombinant strains increase with time. FIG. 5 shows the results for production of lactic acid from biogas.

These studies were done with biogas without upgrading the biogas to remove carbon dioxide. Alternately, the biogas can be cleaned up to remove the carbon dioxide by having a basic purification unit in place. Water scrubbing is a basic method used to remove the carbon dioxide. Pressurized biogas is fed to the bottom of a packed column where water is fed on the top and the absorption process is operated counter-currently.

The cleaned up gas with >90% of methane can be used for growth of strains and lactic acid production.

Examples 8: Effect of pH on Lactic Acid Production

To test the effect of pH on lactic acid production, NMS media was prepared with different buffers. Standard NMS media widely used for methanotrophs growth uses phosphate buffer with a pH of 6.8. NMS media was prepared at pH 4.1, 4.8, 5.8 and 6.8 using acetate or phosphate buffers. NMS media at pH 4.1 and 4.8 was prepared using 50 mM acetate buffer. NMS media at pH 5.8 and 6.8 was prepared using 50 mM phosphate buffer.

The recombinant *Methylococcus capsulatus* with heterologous lactate dehydrogenase gene expressed from a broad host range vector (STB4) was inoculated into 5 ml of each media taken in 30 ml cultures tubes. The tubes were sealed with suba seal and fed with 15 ml of methane mixture using a syringe every 24 hours. Samples were taken every 24 hours and tested for OD at 600 nm. Samples were also centrifuged and the supernatant was assayed for lactic acid using the standard kit according to manufacturer's protocol. The pH of the base media had a distinct effect on the amount of lactic acid produced in the strain (FIG. 6). At the pH of 5.8, the lactic acid production was at least 50% higher when compared to lactic acid production at pH 6.8.

Example 9: Overexpression of Genes for Improved Lactic Acid Production

Gene overexpression targets were cloned into the same base vector (pSB102) together with lactate dehydrogenase genes and expressed in *Methylococcus capsulatus*. In order to clone the additional genes into the vector, a σ54 promoter was amplified from *M. capsulatus* and cloned into pSB102 downstream of the ldh gene using SLIC (Sequence and Ligation Independent Cloning, See Li & Elledge 2007; FIG. 7).

Overexpression gene targets (SEQ ID Nos: 6-15) were amplified from genomic DNA of either *E. coli* or *M. capsulatus* using a 15-20 bp overlap to the vector sequence for cloning by SLIC. These were cloned into pSB102 using SLIC. Positive clones were confirmed by PCR. SLIC was done in a 10 ul reaction according to the following set up: 50-100 ng of vector; 200-400 ng of insert; 1× Buffer 2.1 (NEB); 0.3 μl of T4 DNA Polymerase. All components except the enzyme was added and kept on ice for 5 mins. The enzyme was added to the mixture, mixed well and incubated on ice for 10 mins. 4 ul of the reaction mixture was transformed into *E. coli* and selected on LB/Kan plates to select for true transformants. True transformants were confirmed by PCR.

Confirmed vectors were purified from *E. coli* and conjugated into *M. capsulatus* using the method of Martin and Murrell as outlined above. Positive transformants were selected on NMS agar plates with 30 μg/ml of Kanamycin.

To test the overexpression of the gene targets on lactic acid production, transformants were individually inoculated into 5 ml of standard NMS media in 30 ml cultures tubes together with a control strain that had only the lactate dehydrogenase gene. The tubes were sealed with suba seal and fed with 15 ml of methane mixture using a syringe. Tubes were incubated at 45° C. with 200 rom shaking. At the end of 72 hours, samples were taken and tested for OD at 600 nm and lactic acid production. Samples were centrifuged and the supernatant was assayed for lactic acid using the Megazyme standard kit according to manufacturer's protocol. Table 3 depicts the specific genes when overexpressed with lactate dehydrogenase result in higher levels of lactic acid. SEQ ID 1 when expressed separately in *M. capsulatus* results in at least 20 fold higher activity than the control strain (FIG. 3). When SEQ ID 1 is combined with 11, 17 or 23, a further at least 3 fold improvement in lactic acid levels are seen.

TABLE 3

Improved lactic acid production from gene overexpression of specific target genes

| SEQ IDs | Fold Improvement in lactic acid in *M. capsulatus* |
| --- | --- |
| SEQ ID 7 + SEQ ID 1 | 2.6 |
| SEQ ID 11 + SEQ ID 1 | 3.2 |
| SEQ ID 13 + SEQ ID 1 | 2.4 |
| SEQ ID 15 + SEQ ID 1 | 1.2 |
| SEQ ID 17 + SEQ ID 1 | 3 |
| SEQ ID 19 + SEQ ID 1 | 2.6 |
| SEQ ID 21 + SEQ ID 1 | 1.6 |
| SEQ ID 23 + SEQ ID 1 | 3.8 |
| SEQ ID 1 | 1 |

Example 10: Overexpression of Genes for Improved Lactic Acid Production

To further increase the lactic acid production, overexpression of 2 gene combinations together with lactate dehydrogenase were tested.

To test for 2 gene combinations, the pmxaF promoter was introduced into the overexpression base vector by SLIC. SLIC was done in a 10 ul reaction according to the following set up: 50-100 ng of vector; 200-400 ng of insert; 1× Buffer 2.1 (NEB); 0.3 ul of T4 DNA Polymerase. All components except the enzyme was added and kept on ice for 5 mins. The enzyme was added to the mixture, mixed well and incubated on ice for 10 mins. 4 μl of the reaction mixture was transformed into *E. coli* and selected on LB/Kan plates to select for true transformants. True transformants were confirmed by PCR.

This allowed for an overexpression vector with lactate dehydrogenase cloned under sigma 70 and further two promoters (sigma 54 and pmxF) for expression of other genes. To create combinations, the genes were amplified with 20 bp overlap and introduced sequentially into the overexpression vector using SLIC. Vectors with varying gene combinations (SEQ ID 1, 11, 17; SEQ ID 1, 11, 23; SEQ ID 1, 17, 23) were generated by sequential introduction of the overexpression genes into the base vector. True transformants were confirmed by PCR and isolated from *E. coli*.

Confirmed vectors were purified from *E. coli* and conjugated into *M. capsulatus* using the method of Martin and Murrell as outlined above. Positive transformants were selected on NMS agar plates with 30 ug/ml of Kanamycin. To test the overexpression of the gene targets on lactic acid production, transformants were individually inoculated into 5 ml of standard NMS media in 30 ml cultures tubes together with a control strains that had only the lactate dehydrogenase gene and lactate dehydrogenase genes with the single gene targets. The tubes were sealed with suba seal and fed with 15 ml of methane mixture using a syringe. Tubes were incubated at 45° C. with 200 rom shaking. At the end of 72 hours, samples were taken and tested for OD at 600 nm and lactic acid production. Samples were centrifuged and the supernatant was assayed for lactic acid using the Megazyme standard kit according to manufacturer's protocol.

Recombinant strains that had 2 genes overexpressed had at least two fold and as much as 6 fold improved activity compared to single gene overexpression.

While the invention has been described in detail with reference to preferred embodiments thereof, it will be apparent to one skilled in the art that various changes can be made, and equivalents employed, without departing from the scope of the invention.

I claim:

1. A recombinant methanotrophic bacterium capable of producing lactic acid from organic waste or biogas or methane, comprising
a heterologous nucleic acid or gene encoding for lactate dehydrogenase (ldh) enzyme, having the sequence of SEQ ID NO: 1, 3, or 5, or a combination thereof.

2. The recombinant methanotrophic bacterium as claimed in claim 1, wherein the bacterium is selected from the group consisting of *Methylococcus capsulatus, Methylobacterium extorquens, Methylobacterium organophilum, Methylobacterium mesophilicum, Methylobacterium dichloromethanicum, Methylocella silvestris, Methylosinus trichosporium, Methylobacillus flagellatus* KT, *Methylibium petroleiphilum* PM1, *Methylobacterium nodulans, Methylobacterium populi, Methylobacterium chloromethanicum, Methylacidiphilum infernorum* V4, *Methylophilus methylotrophus, Methylomonas methanica, Methylobacterium rhodesianum* MB 126, *Methylobacter tundripaludum, Methylobacterium* sp. 4-46, *Methylovorus glucosetrophus* SIPS-4, *Mycobacterium smegmatis, Methylobacterium rhodesianum, Methylosinus sporium, Methylosinus trichosporium* Ob3b, *Methylosinus* sp strains, *Methylocella palustris, Methylobacterium fujisawaense, Methylocystis parvus, Methylovulum miyakonense, Methylobacterium rhodinum, Methylocystis echinoides, Methylomonas rubra, Methylococcus thermophilus, Methylobacterium aminovorans, Methylobacterium thiocyanatum, Methylobacterium zatmanii, Acidithiobacillus ferrivorans, Methylobacterium aquaticum, Methylobacterium suomiense, Methylobacterium adhaesivum, Methylobacterium podarium, Methylobacter whittenburyi, Crenothrix polyspora, Clonothrix fusca, Methylobacter bovis, Methylomonas aurantiaca, Methylomonas fodinarum, Methylobacterium variabile, Methylocystis minimus, Methylobacter vinelandii, Methylobacterium hispanicum, Methylomicrobium japanense, Methylococcaceae bacterium*, and *Methylocystis methanolicus.*

3. The recombinant methanotrophic bacterium as claimed in claim 1, wherein the recombinant methanotrophic bacterium further comprises one or more genes for encoding enzyme(s) which are overexpressed selected from the group consisting of glyceraldehyde 3-phosphate dehydrogenase, glucose-6-phosphate isomerase, 2,3-bisphosphoglycerate-independent phosphoglycerate mutase, glycerate 2-kinase, hexulose-6-phosphate synthase, Transaldolase, 6-phosphofructokinase, 2,3-bisphosphoglycerate-dependent phosphoglycerate mutase, enolase, ribulose phosphate 3-epimerase and methanol dehydrogenase or any combination thereof; genes for encoding enzymes(s) which are down-regulated or deleted selected from the group consisting of acetate kinase, acetate synthase, succinyl CoA synthetase, and malate dehydrogenase or any combination thereof, for increasing production of the lactic acid.

4. The recombinant methanotrophic bacterium as claimed in claim 3, wherein the gene(s) encoding enzyme(s), responsible for the increased production of lactic acid by overexpression is the sequence of SEQ ID NO: 7, 9, 11, 13, 15, 17, 19, 21, 23, 25, 27, or 29, or any combination thereof and wherein their corresponding amino acid sequence is SEQ ID NOS: 8, 10, 12, 14, 16, 18, 20, 22, 24, 26, 28, or 30, respectively.

5. The recombinant methanotrophic bacterium as claimed in claim 1, wherein the heterologous nucleic acid or gene encoding for the lactate dehydrogenase enzyme is from a micro-organism selected from the group consisting of *Escherichia coli, Pseudomonas aeruginosa*, and *Pectobacterium carotovorum.*

6. The recombinant methanotrophic bacterium as claimed in claim 1, wherein the lactic acid produced from methane or biogas or organic waste is at least 5 fold higher than that by a wildtype strain under similar conditions.

7. A process for producing lactic acid from organic waste using the recombinant methanotrophic bacterium as claimed in claim 1, said process comprising acts of:
a) receiving organic waste as input;
b) anaerobically digesting the organic waste to biogas;
c) culturing the bacterium in the biogas so generated, for converting the biogas to the lactic acid; and
d) optionally purifying or separating the lactic acid produced from the culture for obtaining the lactic acid.

8. The process as claimed in claim 7, wherein the biogas produced by anaerobically digesting the organic waste is optionally cleaned to remove carbon dioxide and other impurities present in the biogas to obtain methane for producing lactic acid from methane thereafter.

9. A process for producing lactic acid from a carbon source using recombinant methanotrophic bacterium as claimed in claim 1, said process comprising acts of:
a) receiving at least one carbon source selected from the group consisting of biogas or methane as input;
b) culturing the bacterium in the input, thereby converting the input into lactic acid; and
c) optionally purifying or separating the lactic acid produced from the culture for obtaining the lactic acid.

10. The process as claimed in claim 9, wherein the input carbon source has a ratio of methane to carbon dioxide ranging from about 95:5 to about 50:50.

11. The process as claimed in claim 7, wherein temperature maintained for the act of converting methane or biogas to lactic acid is in the range of about 37° C. to about 50° C., and wherein pH maintained during the act of converting methane or biogas to lactic acid is in the range of about 3 to about 7.

12. The process as claimed in claim 7, wherein dissolved oxygen concentration for the act of converting methane or biogas to lactic acid is about <20%.

* * * * *

SEQUENCE LISTING

```
<160> NUMBER OF SEQ ID NOS: 30

<210> SEQ ID NO 1
<211> LENGTH: 990
<212> TYPE: DNA
<213> ORGANISM: Escherichia coli
<220> FEATURE:
<223> OTHER INFORMATION: Lactate dehydrogenase

<400> SEQUENCE: 1
atgaaactcg ccgtttatag cacaaaacag tacgacaaga agtacctgca acaggtgaac      60
gagtcctttg gctttgagct ggaatttttt gactttctgc tgacggaaaa aaccgctaaa     120
actgccaatg gctgcgaagc ggtatgtatt ttcgtaaacg atgacggcag ccgcccggtg     180
ctggaagagc tgaaaaagca cggcgttaaa tatatcgccc tgcgctgtgc cggtttcaat     240
aacgtcgacc ttgacgcggc aaaagaactg gggctgaaag tagtccgtgt tccagcctat     300
gatccagagg ccgttgctga acacgccatc ggtatgatga tgacgctgaa ccgccgtatt     360
caccgcgcgt atcagcgtac ccgtgatgct aacttctctc tggaaggtct gaccggcttt     420
actatgtatg gcaaaacggc aggcgttatc ggtaccggta aaatcggtgt ggcgatgctg     480
cgcattctga aaggttttgg tatgcgtctg ctggcgttcg atccgtatcc aagtgcagcg     540
gcgctggaac tcggtgtgga gtatgtcgat ctgccaaccc tgttctctga atcagacgtt     600
atctctctgc actgcccgct gacaccggaa aactatcatc tgttgaacga agccgccttc     660
gaacagatga aaaatggcgt gatgatcgtc aataccagtc gcggtgcatt gattgattct     720
caggcagcaa ttgaagcgct gaaaaatcag aaaattggtt cgttgggtat ggacgtgtat     780
gagaacgaac gcgatctatt cttttgaagat aaatccaacg acgtgatcca ggatgacgta     840
ttccgtcgcc tgtctgcctg ccacaacgtg ctgtttaccg ggcaccaggc attcctgaca     900
gcagaagctc tgaccagtat ttctcagact acgctgcaaa acttaagcaa tctggaaaaa     960
ggcgaaacct gcccgaacga actggtttaa                                     990

<210> SEQ ID NO 2
<211> LENGTH: 329
<212> TYPE: PRT
<213> ORGANISM: Escherichia coli
<220> FEATURE:
<223> OTHER INFORMATION: Lactate dehydrogenase

<400> SEQUENCE: 2

Met Lys Leu Ala Val Tyr Ser Thr Lys Gln Tyr Asp Lys Lys Tyr Leu
1               5                  10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
        35                  40                  45

Cys Ile Phe Val Asn Asp Asp Gly Ser Arg Pro Val Leu Glu Glu Leu
```

|     |     |     |     | 50  |     |     |     |     | 55  |     |     |     |     | 60  |     |
| --- | --- | --- | --- | --- | --- | --- | --- | --- | --- | --- | --- | --- | --- | --- | --- |

Lys Lys His Gly Val Lys Tyr Ile Ala Leu Arg Cys Ala Gly Phe Asn
65                             70                       75                        80

Asn Val Asp Leu Asp Ala Ala Lys Glu Leu Gly Leu Lys Val Val Arg
                   85                      90                      95

Val Pro Ala Tyr Asp Pro Glu Ala Val Ala Glu His Ala Ile Gly Met
               100                    105                  110

Met Met Thr Leu Asn Arg Arg Ile His Arg Ala Tyr Gln Arg Thr Arg
          115                   120                  125

Asp Ala Asn Phe Ser Leu Glu Gly Leu Thr Gly Phe Thr Met Tyr Gly
 130                    135                  140

Lys Thr Ala Gly Val Ile Gly Thr Gly Lys Ile Gly Val Ala Met Leu
145                    150                  155                160

Arg Ile Leu Lys Gly Phe Gly Met Arg Leu Leu Ala Phe Asp Pro Tyr
               165                    170                175

Pro Ser Ala Ala Ala Leu Glu Leu Gly Val Glu Tyr Val Asp Leu Pro
          180                   185                  190

Thr Leu Phe Ser Glu Ser Asp Val Ile Ser Leu His Cys Pro Leu Thr
         195                   200                  205

Pro Glu Asn Tyr His Leu Leu Asn Glu Ala Ala Phe Glu Gln Met Lys
 210                   215                  220

Asn Gly Val Met Ile Val Asn Thr Ser Arg Gly Ala Leu Ile Asp Ser
225                    230                  235                240

Gln Ala Ala Ile Glu Ala Leu Lys Asn Gln Lys Ile Gly Ser Leu Gly
               245                    250                255

Met Asp Val Tyr Glu Asn Glu Arg Asp Leu Phe Phe Glu Asp Lys Ser
          260                   265                  270

Asn Asp Val Ile Gln Asp Val Phe Arg Arg Leu Ser Ala Cys His
         275                   280                  285

Asn Val Leu Phe Thr Gly His Gln Ala Phe Leu Thr Ala Glu Ala Leu
 290                   295                  300

Thr Ser Ile Ser Gln Thr Thr Leu Gln Asn Leu Ser Asn Leu Glu Lys
305                    310                  315                320

Gly Glu Thr Cys Pro Asn Glu Leu Val
               325

```
<210> SEQ ID NO 3
<211> LENGTH: 1286
<212> TYPE: DNA
<213> ORGANISM: Pseudomonas aeruginosa
<220> FEATURE:
<223> OTHER INFORMATION: Lactate dehydrogenase

<400> SEQUENCE: 3
gaccagcgaa accctgctca agcagaacga tccggcggcg gccgcggccc tggacgagct      60
ggacaaggcc atcgaggccc tggccgacac tgcctcggcc accacccacc tgtcctccac     120
cagcctcgac tccagcgaac tctgaccatg cgcatcctgt tcttcagcag ccaggcctac     180
gacagcgaga gcttccaggc cagcaaccac cggcacggct cgaactgca cttccagcag     240 gcccacctgc aggcggacac ggcggtcctc gcccagggct cgaagtagt ctgcgccttc     300 gtcaacgacg acctctcgcg gccggtgctg aacgcctgg cggccggcgg cacgcgcctg     360
gtcgccctgc gtcggccgg ctacaaccac gtcgacctgg ccgccgccga agcgctcggc     420
ctgccggtgg tgcacgtccc ggcctattcg ccgcacgctg tcgccgagca cgcggtcggc     480
```

```
ctgatcctga cgctcaaccg gcgcctgcac cgcgcctaca accggacccg cgagggcgat      540
ttctcgctgc atgggctgac cggcttcgac ctccacggca aacgcgtcgg agtgatcggc      600
accggacaga tcgcgagac  cttcgcccgc atcatggccg gcttcggctg cgagctgctg      660
gcctacgatc cttatcccaa tccgcgcatc caagcactcg gcggccgcta cctggcgctc      720
gacgccctgc tcgccgagtc cgacatcgtc agcctgcatt gcccgctgac cgccgacacc      780
cgccacctca tcgacgcgca cgcgctggcg acgatgaaac ccggcgcgat gctgatcaat      840
accggccgtg cgccctggt  gaacgccgcg cgcgctgatcg aggcgctgaa gagcggacaa     900
ctgggctacc tcggcctcga tgtctatgaa gaggaagcgg atatcttttt cgaggatcgc      960
tccgaccagc ccctgcagga tgacgtgctg gcacgcctgc tgagcttccc caacgtggtg     1020
gtgacggccc accaggcctt ccttacccgc gaggccctgg cggcgatcgc cgacaccacc     1080
ctggacaaca tcgccgcctg caggacgggg acgccgcgca atcgggtccg ggcctgatgg     1140
cgtggtagca tgcgcggctg attggaggct ccatggctga acacgatttc cgttacaccc     1200
tgctcaaccc gcaatacacc ctcaacgaat gccgcgcgct ctccccgggg cgctaccagg     1260
tcaccggcac cggcggctcg atcaag                                         1286
```

<210> SEQ ID NO 4
<211> LENGTH: 329
<212> TYPE: PRT
<213> ORGANISM: Pseudomonas aeruginosa
<220> FEATURE:
<223> OTHER INFORMATION: Lactate dehydrogenase

<400> SEQUENCE: 4

```
Met Arg Ile Leu Phe Phe Ser Ser Gln Ala Tyr Asp Ser Glu Ser Phe
1               5                   10                  15

Gln Ala Ser Asn His Arg His Gly Phe Glu Leu His Phe Gln Gln Ala
            20                  25                  30

His Leu Gln Ala Asp Thr Ala Val Leu Ala Gln Gly Phe Glu Val Val
        35                  40                  45

Cys Ala Phe Val Asn Asp Asp Leu Ser Arg Pro Val Leu Glu Arg Leu
    50                  55                  60

Ala Ala Gly Gly Thr Arg Leu Val Ala Leu Arg Ser Ala Gly Tyr Asn
65                  70                  75                  80

His Val Asp Leu Ala Ala Ala Glu Ala Leu Gly Leu Pro Val Val His
                85                  90                  95

Val Pro Ala Tyr Ser Pro His Ala Val Ala Glu His Ala Val Gly Leu
            100                 105                 110

Ile Leu Thr Leu Asn Arg Arg Leu His Arg Ala Tyr Asn Arg Thr Arg
        115                 120                 125

Glu Gly Asp Phe Ser Leu His Gly Leu Thr Gly Phe Asp Leu His Gly
    130                 135                 140

Lys Arg Val Gly Val Ile Gly Thr Gly Gln Ile Gly Glu Thr Phe Ala
145                 150                 155                 160

Arg Ile Met Ala Gly Phe Gly Cys Glu Leu Leu Ala Tyr Asp Pro Tyr
                165                 170                 175

Pro Asn Pro Arg Ile Gln Ala Leu Gly Gly Arg Tyr Leu Ala Leu Asp
            180                 185                 190

Ala Leu Leu Ala Glu Ser Asp Ile Val Ser Leu His Cys Pro Leu Thr
        195                 200                 205

Ala Asp Thr Arg His Leu Ile Asp Ala Gln Arg Leu Ala Thr Met Lys
    210                 215                 220
```

Pro Gly Ala Met Leu Ile Asn Thr Gly Arg Gly Ala Leu Val Asn Ala
225                 230                 235                 240

Ala Ala Leu Ile Glu Ala Leu Lys Ser Gly Gln Leu Gly Tyr Leu Gly
            245                 250                 255

Leu Asp Val Tyr Glu Glu Glu Asp Ile Phe Phe Glu Asp Arg Ser
            260                 265                 270

Asp Gln Pro Leu Gln Asp Val Leu Ala Arg Leu Leu Ser Phe Pro
        275                 280                 285

Asn Val Val Thr Ala His Gln Ala Phe Leu Thr Arg Glu Ala Leu
    290                 295                 300

Ala Ala Ile Ala Asp Thr Thr Leu Asp Asn Ile Ala Ala Trp Gln Asp
305                 310                 315                 320

Gly Thr Pro Arg Asn Arg Val Arg Ala
                325

<210> SEQ ID NO 5
<211> LENGTH: 993
<212> TYPE: DNA
<213> ORGANISM: Pectobacterium carotovorum
<220> FEATURE:
<223> OTHER INFORMATION: Lactate dehydrogenase

<400> SEQUENCE: 5

```
atgaaactgg caatttacag cacgaagcag tatgaccgta aatatctgga acaggtcaat    60
cagcagtttg gctatgagct agagtttttt gattttatgc tgacatcacg caccgcaaaa   120
accgccgcag gctgtcaggc cgtctgcatc tttgtgaacg atgacggtgg cgcgaagtg    180
ttgaccgaac tggctgcgtt gggcattaaa acgctggcgc tgcgctgtgc aggctttaac   240
aatgtcgatt tggaagccgc taaggagctg gtatcagcg tggtacgcgt tcccgcgtat    300
tcccccgaag ccgtcgccga acatgcagtc ggcctgatgc tgacgcttaa ccgccgcatt   360
caccgtgcct atcagcgtac tcgcgacgcg aacttctctc tggaaggatt gattggcttc   420
aatatgcaca accggacggc gggcattatc ggcaccggaa aaatcggcat cgccaccatg   480
cgcatcctga aaggctttgg catgcgactg ctggccttcg atccctaccc aaacccgcag   540
gccttggaat taggggcgga gtacgtcgat ctaaaaacgc tgtatgccaa tgcggacgtc   600
atctccctgc actgcccgct gacgccggag aatcatcatc tgctgaatca ggcggccttt   660
gcacaaatga aaaacggcgt catgatcgtc aataccagcc gtggtggact aatcgactca   720
caggccgcta tcgacgcgtt gaagcaacag aaaattggcg cgctgggtat ggacgtttat   780
gaaaacgagc gcgatctctt ctttgccgat aaatccaacg atgtgattca ggacgatatt   840
ttccgccgct atccgcgtg ccacaacgtg ctatttaccg ggcatcaggc gttcctgacg   900
gaagaagcgc taatcagcat ttcccaaacc acgctacaga acttgaaaga cctcagccag   960
aacgcgcctt gcgcaaatct ggttacctct taa                                993
```

<210> SEQ ID NO 6
<211> LENGTH: 330
<212> TYPE: PRT
<213> ORGANISM: Pectobacterium carotovorum
<220> FEATURE:
<223> OTHER INFORMATION: Lactate dehydrogenase

<400> SEQUENCE: 6

Met Lys Leu Ala Ile Tyr Ser Thr Lys Gln Tyr Asp Arg Lys Tyr Leu
1               5                   10                  15

```
Glu Gln Val Asn Gln Gln Phe Gly Tyr Glu Leu Glu Phe Asp Phe
             20                  25                  30

Met Leu Thr Ser Arg Thr Ala Lys Thr Ala Ala Gly Cys Gln Ala Val
         35                  40                  45

Cys Ile Phe Val Asn Asp Gly Gly Arg Glu Val Leu Thr Glu Leu
 50                  55                  60

Ala Ala Leu Gly Ile Lys Thr Leu Ala Leu Arg Cys Ala Gly Phe Asn
 65                  70                  75                  80

Asn Val Asp Leu Glu Ala Ala Lys Glu Leu Gly Ile Ser Val Val Arg
                 85                  90                  95

Val Pro Ala Tyr Ser Pro Glu Ala Val Ala Glu His Ala Val Gly Leu
             100                 105                 110

Met Leu Thr Leu Asn Arg Arg Ile His Arg Ala Tyr Gln Arg Thr Arg
             115                 120                 125

Asp Ala Asn Phe Ser Leu Glu Gly Leu Ile Gly Phe Asn Met His Asn
             130                 135                 140

Arg Thr Ala Gly Ile Ile Gly Thr Gly Lys Ile Gly Ile Ala Thr Met
145                 150                 155                 160

Arg Ile Leu Lys Gly Phe Gly Met Arg Leu Leu Ala Phe Asp Pro Tyr
                 165                 170                 175

Pro Asn Pro Gln Ala Leu Glu Leu Gly Ala Glu Tyr Val Asp Leu Lys
             180                 185                 190

Thr Leu Tyr Ala Asn Ala Asp Val Ile Ser Leu His Cys Pro Leu Thr
             195                 200                 205

Pro Glu Asn His His Leu Leu Asn Gln Ala Ala Phe Ala Gln Met Lys
 210                 215                 220

Asn Gly Val Met Ile Val Asn Thr Ser Arg Gly Gly Leu Ile Asp Ser
225                 230                 235                 240

Gln Ala Ala Ile Asp Ala Leu Lys Gln Gln Lys Ile Gly Ala Leu Gly
                 245                 250                 255

Met Asp Val Tyr Glu Asn Glu Arg Asp Leu Phe Phe Ala Asp Lys Ser
             260                 265                 270

Asn Asp Val Ile Gln Asp Ile Phe Arg Arg Leu Ser Ala Cys His
             275                 280                 285

Asn Val Leu Phe Thr Gly His Gln Ala Phe Leu Thr Glu Glu Ala Leu
 290                 295                 300

Ile Ser Ile Ser Gln Thr Thr Leu Gln Asn Leu Lys Asp Leu Ser Gln
305                 310                 315                 320

Asn Ala Pro Cys Ala Asn Leu Val Thr Ser
                 325                 330
```

<210> SEQ ID NO 7
<211> LENGTH: 648
<212> TYPE: DNA
<213> ORGANISM: Methylococcus capsulatus
<220> FEATURE:
<223> OTHER INFORMATION: Hexulose-6-phosphate synthase

<400> SEQUENCE: 7

```
atgccaagac cattgattca gctcgccctg gacacgctgg acatcccgca gaccctgaag     60
ctcgcaagcc tcaccgcgcc ctatgtcgat atcttcgaaa tcggcacccc cagcatcaag    120
cacaacggca tcgccctggt gaaggagttc aaaaaacgct cccccaacaa gctgctcctg    180
gtcgacctca aaaccatgga cgccggtgaa tacgaagcca cccccttctt cgccgccggc    240
gccgacatca ccaccgtcct cggcgtcgca ggactggcca ccatcaaggg cgtcatcaac    300
```

```
gccgccaaca agcacaacgc cgaggtccag gtcgacctga tcaacgtccc cgacaaggcc      360
gcctgcgccc gtgagtccgc caaggccggc gcccagatcg tcggcatcca caccggcctc      420
gacgcccagg ccgccggcca gacccccttc gccgacctcc aggccatcgc caagctcggc      480
ctccccgtcc gcatctccgt cgccggcggc atcaaggcct ccaccgccca acaggtcgtc      540
aaaaccggtg ccaacatcat cgtcgtcgga gccgccatct acggcgccgc ctcccccgcc      600
gatgccgcgc gcgaaatcta cgaacaggtc gtcgccgctt ccgcctaa                   648
```

```
<210> SEQ ID NO 8
<211> LENGTH: 215
<212> TYPE: PRT
<213> ORGANISM: Methylococcus capsulatus
<220> FEATURE:
<223> OTHER INFORMATION: Hexulose-6-phosphate synthase

<400> SEQUENCE: 8

Met Ala Arg Pro Leu Ile Gln Leu Ala Leu Asp Thr Leu Asp Ile Pro
1               5                   10                  15

Gln Thr Leu Lys Leu Ala Ser Leu Thr Ala Pro Tyr Val Asp Ile Phe
            20                  25                  30

Glu Ile Gly Thr Pro Ser Ile Lys His Asn Gly Ile Ala Leu Val Lys
        35                  40                  45

Glu Phe Lys Lys Arg Phe Pro Asn Lys Leu Leu Leu Val Asp Leu Lys
    50                  55                  60

Thr Met Asp Ala Gly Glu Tyr Glu Ala Thr Pro Phe Phe Ala Ala Gly
65                  70                  75                  80

Ala Asp Ile Thr Thr Val Leu Gly Val Ala Gly Leu Ala Thr Ile Lys
                85                  90                  95

Gly Val Ile Asn Ala Ala Asn Lys His Asn Ala Glu Val Gln Val Asp
            100                 105                 110

Leu Ile Asn Val Pro Asp Lys Ala Ala Cys Ala Arg Glu Ser Ala Lys
        115                 120                 125

Ala Gly Ala Gln Ile Val Gly Ile His Thr Gly Leu Asp Ala Gln Ala
    130                 135                 140

Ala Gly Gln Thr Pro Phe Ala Asp Leu Gln Ala Ile Ala Lys Leu Gly
145                 150                 155                 160

Leu Pro Val Arg Ile Ser Val Ala Gly Gly Ile Lys Ala Ser Thr Ala
                165                 170                 175

Gln Gln Val Val Lys Thr Gly Ala Asn Ile Ile Val Gly Ala Ala
            180                 185                 190

Ile Tyr Gly Ala Ala Ser Pro Ala Asp Ala Ala Arg Glu Ile Tyr Glu
        195                 200                 205

Gln Val Val Ala Ala Ser Ala
    210                 215
```

```
<210> SEQ ID NO 9
<211> LENGTH: 1263
<212> TYPE: DNA
<213> ORGANISM: Methylococcus capsulatus
<220> FEATURE:
<223> OTHER INFORMATION: Phospho-fructo-kinase

<400> SEQUENCE: 9
atggcggcgc ggaatgcttt ctatgcccag tccggcggtg tgaccgccgt tatcaatgca      60
tcggcctgcg gcgtgctgga gaccgcccgg cagtatcccg accgtatcgg cacggtttac     120
```

```
gccgggcgta acggcatcgt cggtgcactg accgaggacc tgatcgatac cgggcaggag      180
agcgccgaag ccatcgccgc attgcgccac actccctccg ggcgttcgg ttcctgccgc       240 tacaagctca aagggctgga ggagaaccgg gcccagtacg aacggttgat cgaggtcttc      300
cgcgcccacg acatcggcta tttcttctac aacggcggcg gggattccgc cgatacctgt     360
ctgaaagtct cccagctttc cgagaaattg ggttatccgt tgcaggccgt ccatattccg      420
aagacggtgg acaacgacct gccgatcacc gactgctgtc cggggttcgg ttcggtcgcc     480
aagtacatag cggtatcggt acgcgaggcg agtttcgacg tacgctccat ggctgcgact     540
tccacctgca tcttcgtgct ggaagtcatg ggccgccacg cgggctggat cgccgccgcc    600
ggcggtctgg cgagtgacga gcggcatgag ctggctctgg tcatcttgtt tcccgaacag     660
gtgttcgacc cggaacggtt tctccggggcg gtggacgaaa aggtccggtc acatggctat    720
tgttcggtcg tggtgtcgga gggcattagg ggcgcggatg caggttcgt cgccgaatcc     780 ggcagccggg acgtgttcgg gcatgctcgg ctcggtgggg tggcgccggt catcgccgac    840
ctgatcaagg agcgcctggg ttacaaatac cactgggccg tcgccgatta cctgcagcgc    900
gcggcccggc acatcgcctc cgcacggat gtcgagcagg cctatgcggt ggggaaggcg     960
ggcgtcgaga tggctctgaa agggctcagc gccgtgatgc cggccatcgt gcgcacctcg    1020
gattcgcctt accgttggga aatcacggcc gccagtctgg cggaggtggc caacgtcgaa    1080
aagaaaatgc ccctcgaatt catcagcgcc gacggtttcg gcatcaccga ggcctgccgc    1140
cggtacctcc ggcctctgat cgagggcgag gactaccctc cctatgccgg cggtttgccg    1200
gattatgtga cattgtgcaa tgtcgctgtc ccgaaaaaac tggccgcttc gttcagcgtc     1260
tga                                                                    1263
```

<210> SEQ ID NO 10
<211> LENGTH: 420
<212> TYPE: PRT
<213> ORGANISM: Methylococcus capsulatus
<220> FEATURE:
<223> OTHER INFORMATION: Phospho-fructo-kinase

<400> SEQUENCE: 10

```
Met Ala Ala Arg Asn Ala Phe Tyr Ala Gln Ser Gly Gly Val Thr Ala
1               5                   10                  15

Val Ile Asn Ala Ser Ala Cys Gly Val Leu Glu Thr Ala Arg Gln Tyr
            20                  25                  30

Pro Asp Arg Ile Gly Thr Val Tyr Ala Gly Arg Asn Gly Ile Val Gly
        35                  40                  45

Ala Leu Thr Glu Asp Leu Ile Asp Thr Gly Gln Glu Ser Ala Glu Ala
    50                  55                  60

Ile Ala Ala Leu Arg His Thr Pro Ser Gly Ala Phe Gly Ser Cys Arg
65                  70                  75                  80

Tyr Lys Leu Lys Gly Leu Glu Glu Asn Arg Ala Gln Tyr Glu Arg Leu
                85                  90                  95

Ile Glu Val Phe Arg Ala His Asp Ile Gly Tyr Phe Tyr Asn Gly
            100                 105                 110

Gly Gly Asp Ser Ala Asp Thr Cys Leu Lys Val Ser Gln Leu Ser Glu
        115                 120                 125

Lys Leu Gly Tyr Pro Leu Gln Ala Val His Ile Pro Lys Thr Val Asp
    130                 135                 140

Asn Asp Leu Pro Ile Thr Asp Cys Cys Pro Gly Phe Gly Ser Val Ala
145                 150                 155                 160
```

Lys Tyr Ile Ala Val Ser Val Arg Glu Ala Ser Phe Asp Val Arg Ser
            165                 170                 175

Met Ala Ala Thr Ser Thr Cys Ile Phe Val Leu Glu Val Met Gly Arg
        180                 185                 190

His Ala Gly Trp Ile Ala Ala Gly Gly Leu Ala Ser Asp Glu Arg
        195                 200                 205

His Glu Leu Ala Leu Val Ile Leu Phe Pro Glu Gln Val Phe Asp Pro
    210                 215                 220

Glu Arg Phe Leu Arg Ala Val Asp Glu Lys Val Arg Ser His Gly Tyr
225                 230                 235                 240

Cys Ser Val Val Ser Glu Gly Ile Arg Gly Ala Asp Gly Arg Phe
                245                 250                 255

Val Ala Glu Ser Gly Ser Arg Asp Val Phe Gly His Ala Arg Leu Gly
            260                 265                 270

Gly Val Ala Pro Val Ile Ala Asp Leu Ile Lys Glu Arg Leu Gly Tyr
        275                 280                 285

Lys Tyr His Trp Ala Val Ala Asp Tyr Leu Gln Arg Ala Ala Arg His
    290                 295                 300

Ile Ala Ser Arg Thr Asp Val Glu Gln Ala Tyr Ala Val Gly Lys Ala
305                 310                 315                 320

Gly Val Glu Met Ala Leu Lys Gly Leu Ser Ala Val Met Pro Ala Ile
                325                 330                 335

Val Arg Thr Ser Asp Ser Pro Tyr Arg Trp Glu Ile Thr Ala Ala Ser
            340                 345                 350

Leu Ala Glu Val Ala Asn Val Glu Lys Lys Met Pro Leu Glu Phe Ile
        355                 360                 365

Ser Ala Asp Gly Phe Gly Ile Thr Glu Ala Cys Arg Arg Tyr Leu Arg
    370                 375                 380

Pro Leu Ile Glu Gly Glu Asp Tyr Pro Pro Tyr Ala Gly Gly Leu Pro
385                 390                 395                 400

Asp Tyr Val Thr Leu Cys Asn Val Ala Val Pro Lys Lys Leu Ala Ala
                405                 410                 415

Ser Phe Ser Val
            420

<210> SEQ ID NO 11
<211> LENGTH: 1641
<212> TYPE: DNA
<213> ORGANISM: Methylococcus capsulatus
<220> FEATURE:
<223> OTHER INFORMATION: Glucose-6-phosphate isomerase

<400> SEQUENCE: 11
atgccacaat cgaccgacct tcccgcctgg cggactcttt ccgaacactt caagaccatt    60 gcccccgcc atatgcgcga catgttcgcc gacgatccgg ggcgtttcga ggccttttcc    120
gtccggctgg gcgatctgct gttcgactac tccaagaacc ggatcacccg gaaaccgtc    180 gcgacgctga tccagctcgc cgaggaggcc ggtctgcgtg aaaagatcga tgccatgttt    240
cggggcgaac ggctcaacgt cacggagaac cgtgcggtgc ttcatgtcgc cctccgcaat    300
cgctccaacc gtccgattcg ggtcgacggc aaagacgtca tgccggaggt caaccgcgtt    360
ctcgaccgca tgcgccgctt ctctcagtcg gtccgcacgg gagaatggcg cggcgcgacc    420
ggcaaggcca tcaccgatgt ggtcaacatc ggcatcggcg gtccgacct gggcccaaag    480 atggtggtca aggcgctgca gccttacgca gacccgcggc tgcgcgcgca cttcgtctcc    540

```
aacgtcgacg aatccgacct ggtcgagatc ctcaggccgc tgaatccgga aaccacgctg    600
ttcgtcgtcg cctccaagac tttcacgacc caggagacca tgaccaacgg ccgttcggcc    660
cgcgcctggt tcctggaacg catttcggac gaatccgcca tcgcccgtca cttcgtcgct    720
atttcgacca accggaacaa ggtcgccgaa ttcggcatcg atccccgcaa catgttcgaa    780
ttctgggact gggtaggtgg gcgctattcg ctgtggtcgg ccatcggcct ccccatcgcg    840
ctgagcgttg gcatggaccg cttcgaggaa ctgctcgaag gcgcccattt cgtcgatgaa    900
catttccgca ccgccccgtt cgaacgcaac atcccggtgc tgatgggcct cctgggcatt    960
tggtacatca atttcttcgg cgcccagagc catgccgtgc tgccgtatga tcagtacttg   1020
gaggatctgc cagcccatct tcagcaggcc gacatggaaa gcaacggcaa aaccgtcgac   1080
gtggaaggcc ggccggtgaa ctactccacc ggccccgtca tcttcggcca gcccggcacc   1140
aacggccagc atgctttcta ccagttgctc catcaaggca gcatgctggt gccctgtgat   1200
ttccttgcgg cggcggaaag ccatcaccct ctggccgaac accacgacat cctgatctcc   1260
aatttcctgg ctcaaaccga agcgttgatg cggggacgca ccacggatga ggccagacag   1320
gagatcgcct cggaagaact gccccccgaa cgcctcgaag cgctggcggc cgccaagacc   1380
ttccccggca acaaaccgac caacagcttc ctgtaccgtc ggctcgaccc ccatacccctg   1440 ggcatgctga tcgccttgta cgaacacaag attttcaccc agggcgtgat ctggtacatc   1500
aactccttcg accagatggg cgttgaactc ggcaaacagc tggcgaagac cattctggcc   1560
gaactccccg cgatgccccc ggtcgcttcg cacgatgcat ccaccaacgg cctgatccga   1620
tacttcaagt cgctgcgctg a                                            1641
```

```
<210> SEQ ID NO 12
<211> LENGTH: 546
<212> TYPE: PRT
<213> ORGANISM: Methylococcus capsulatus
<220> FEATURE:
<223> OTHER INFORMATION: Glucose-6-phosphate isomerase

<400> SEQUENCE: 12

Met Pro Gln Ser Thr Asp Leu Pro Ala Trp Arg Thr Leu Ser Glu His
1               5                   10                  15

Phe Lys Thr Ile Ala Pro Arg His Met Arg Asp Met Phe Ala Asp Asp
            20                  25                  30

Pro Gly Arg Phe Glu Ala Phe Ser Val Arg Leu Gly Asp Leu Leu Phe
        35                  40                  45

Asp Tyr Ser Lys Asn Arg Ile Thr Arg Glu Thr Val Ala Thr Leu Ile
    50                  55                  60

Gln Leu Ala Glu Glu Ala Gly Leu Arg Glu Lys Ile Asp Ala Met Phe
65                  70                  75                  80

Arg Gly Glu Arg Leu Asn Val Thr Glu Asn Arg Ala Val Leu His Val
                85                  90                  95

Ala Leu Arg Asn Arg Ser Asn Arg Pro Ile Arg Val Asp Gly Lys Asp
            100                 105                 110

Val Met Pro Glu Val Asn Arg Val Leu Asp Arg Met Arg Arg Phe Ser
        115                 120                 125

Gln Ser Val Arg Thr Gly Glu Trp Arg Gly Ala Thr Gly Lys Ala Ile
    130                 135                 140

Thr Asp Val Val Asn Ile Gly Ile Gly Gly Ser Asp Leu Gly Pro Lys
145                 150                 155                 160
```

```
Met Val Val Lys Ala Leu Gln Pro Tyr Ala Asp Pro Arg Leu Arg Ala
                165                 170                 175

His Phe Val Ser Asn Val Asp Glu Ser Asp Leu Val Glu Ile Leu Arg
            180                 185                 190

Pro Leu Asn Pro Glu Thr Thr Leu Phe Val Val Ala Ser Lys Thr Phe
        195                 200                 205

Thr Thr Gln Glu Thr Met Thr Asn Gly Arg Ser Ala Arg Ala Trp Phe
    210                 215                 220

Leu Glu Arg Ile Ser Asp Glu Ser Ala Ile Ala Arg His Phe Val Ala
225                 230                 235                 240

Ile Ser Thr Asn Arg Asn Lys Val Ala Glu Phe Gly Ile Asp Pro Arg
                245                 250                 255

Asn Met Phe Glu Phe Trp Asp Trp Val Gly Arg Tyr Ser Leu Trp
            260                 265                 270

Ser Ala Ile Gly Leu Pro Ile Ala Leu Ser Val Gly Met Asp Arg Phe
            275                 280                 285

Glu Glu Leu Leu Glu Gly Ala His Phe Val Asp Glu His Phe Arg Thr
        290                 295                 300

Ala Pro Phe Glu Arg Asn Ile Pro Val Leu Met Gly Leu Leu Gly Ile
305                 310                 315                 320

Trp Tyr Ile Asn Phe Phe Gly Ala Gln Ser His Ala Val Leu Pro Tyr
                325                 330                 335

Asp Gln Tyr Leu Glu Asp Leu Pro Ala His Leu Gln Ala Asp Met
            340                 345                 350

Glu Ser Asn Gly Lys Thr Val Asp Val Glu Gly Arg Pro Val Asn Tyr
        355                 360                 365

Ser Thr Gly Pro Val Ile Phe Gly Gln Pro Gly Thr Asn Gly Gln His
    370                 375                 380

Ala Phe Tyr Gln Leu Leu His Gln Gly Ser Met Leu Val Pro Cys Asp
385                 390                 395                 400

Phe Leu Ala Ala Ala Glu Ser His His Pro Leu Ala Glu His His Asp
                405                 410                 415

Ile Leu Ile Ser Asn Phe Leu Ala Gln Thr Glu Ala Leu Met Arg Gly
            420                 425                 430

Arg Thr Thr Asp Glu Ala Arg Gln Glu Ile Ala Ser Glu Glu Leu Pro
        435                 440                 445

Pro Glu Arg Leu Glu Ala Leu Ala Ala Lys Thr Phe Pro Gly Asn
    450                 455                 460

Lys Pro Thr Asn Ser Phe Leu Tyr Arg Arg Leu Asp Pro His Thr Leu
465                 470                 475                 480

Gly Met Leu Ile Ala Leu Tyr Glu His Lys Ile Phe Thr Gln Gly Val
                485                 490                 495

Ile Trp Tyr Ile Asn Ser Phe Asp Gln Met Gly Val Glu Leu Gly Lys
            500                 505                 510

Gln Leu Ala Lys Thr Ile Leu Ala Glu Leu Pro Gly Asp Ala Pro Val
        515                 520                 525

Ala Ser His Asp Ala Ser Thr Asn Gly Leu Ile Arg Tyr Phe Lys Ser
530                 535                 540

Leu Arg
545

<210> SEQ ID NO 13
<211> LENGTH: 990
<212> TYPE: DNA
```

<213> ORGANISM: Methylococcus capsulatus
<220> FEATURE:
<223> OTHER INFORMATION: Transaldolase

<400> SEQUENCE: 13

```
atgtcgaaaa acctgcttga ccaactccgc gaagtcaccg tcgtcgtcgc cgataccgga     60
gacatcgaag cgatcgagaa attcaagcca cgtgacgcga ccaccaatcc ctcgctcatc    120
accgccgcag cccaaatgcc gcaataccag gatatcgtcg acgataccct gaaaggtgcg    180
aggcagactc tgggacctgg cgcatcggcc gctcaagtgg cgaatcgcgc tttcgatcgt    240
ctggccgtct ctttcggctt gaagatcctg cagattatcg aaggccgcgt tccaccgaa     300
gtggatgccc gcctttccta cgacaccgaa ggcaccatcg agaaggctcg cgaaatcatc    360
aagcaatacg aagccgccgg cgtttccaaa gagcgtgtcc tgatcaagat cgccgccact    420
tgggagggca tcgaggccgc cgccgtactg gaaaaggagg gaatccactg caacctgacg    480
ctgttgttcg gtctgcatca ggccatcgcc tgcgccgaga acggcatcac cctgatttcc    540
cccttcgtcg gtcgtatcct cgactggtac aagaaggaca ccggtcgcga atcctatgcg    600
ccgcatgaag atccaggcgt cctgtccgtg acccagatct acaactacta caagaagttc    660
ggttacaaga ccgaggtcat gggcgccagc ttccgcaaca tcggcgaaat caccgaactg    720
gccggctgcg acctgctgac catcgcacct tcactgctgg ccgaactgca agccaccgaa    780
ggcgaactgc cgcgtaagct ggatcccgcc aaagcgaagg actacccgat cgagaaaatc    840
cacgtcaaca atacaccttc gacaagatg catgcggaaa accgcatggc caccgagaaa    900
ctggaagaag gcattcaagg ctttaccaag gcactcgagc agctggagaa gttgctggcc    960
gatcgcctgg cccatctgga agcggcataa                                    990
```

<210> SEQ ID NO 14
<211> LENGTH: 329
<212> TYPE: PRT
<213> ORGANISM: Methylococcus capsulatus
<220> FEATURE:
<223> OTHER INFORMATION: Transaldolase

<400> SEQUENCE: 14

```
Met Ser Lys Asn Leu Leu Asp Gln Leu Arg Glu Val Thr Val Val Val
1               5                   10                  15

Ala Asp Thr Gly Asp Ile Glu Ala Ile Glu Lys Phe Lys Pro Arg Asp
            20                  25                  30

Ala Thr Thr Asn Pro Ser Leu Ile Thr Ala Ala Gln Met Pro Gln
        35                  40                  45

Tyr Gln Asp Ile Val Asp Asp Thr Leu Lys Gly Ala Arg Gln Thr Leu
    50                  55                  60

Gly Pro Gly Ala Ser Ala Ala Gln Val Ala Asn Arg Ala Phe Asp Arg
65                  70                  75                  80

Leu Ala Val Ser Phe Gly Leu Lys Ile Leu Gln Ile Ile Glu Gly Arg
                85                  90                  95

Val Ser Thr Glu Val Asp Ala Arg Leu Ser Tyr Asp Thr Glu Gly Thr
            100                 105                 110

Ile Glu Lys Ala Arg Glu Ile Ile Lys Gln Tyr Glu Ala Ala Gly Val
        115                 120                 125

Ser Lys Glu Arg Val Leu Ile Lys Ile Ala Ala Thr Trp Glu Gly Ile
    130                 135                 140

Glu Ala Ala Ala Val Leu Glu Lys Glu Gly Ile His Cys Asn Leu Thr
145                 150                 155                 160
```

Leu Leu Phe Gly Leu His Gln Ala Ile Ala Cys Ala Glu Asn Gly Ile
            165                 170                 175

Thr Leu Ile Ser Pro Phe Val Gly Arg Ile Leu Asp Trp Tyr Lys Lys
            180                 185                 190

Asp Thr Gly Arg Glu Ser Tyr Ala Pro His Glu Asp Pro Gly Val Leu
            195                 200                 205

Ser Val Thr Gln Ile Tyr Asn Tyr Tyr Lys Lys Phe Gly Tyr Lys Thr
    210                 215                 220

Glu Val Met Gly Ala Ser Phe Arg Asn Ile Gly Glu Ile Thr Glu Leu
225                 230                 235                 240

Ala Gly Cys Asp Leu Leu Thr Ile Ala Pro Ser Leu Leu Ala Glu Leu
            245                 250                 255

Gln Ala Thr Glu Gly Glu Leu Pro Arg Lys Leu Asp Pro Ala Lys Ala
            260                 265                 270

Lys Asp Tyr Pro Ile Glu Lys Ile His Val Asn Lys Tyr Thr Phe Asp
            275                 280                 285

Lys Met His Ala Glu Asn Arg Met Ala Thr Glu Lys Leu Glu Glu Gly
        290                 295                 300

Ile Gln Gly Phe Thr Lys Ala Leu Glu Gln Leu Glu Lys Leu Leu Ala
305                 310                 315                 320

Asp Arg Leu Ala His Leu Glu Ala Ala
            325

<210> SEQ ID NO 15
<211> LENGTH: 753
<212> TYPE: DNA
<213> ORGANISM: Escherichia coli
<220> FEATURE:
<223> OTHER INFORMATION: 2,3-bisphosphoglycerate-dependent
      phosphoglycerate mutase

<400> SEQUENCE: 15
atggctgtaa ctaagctggt tctggttcgt catggcgaaa gtcagtggaa caaagaaaac      60
cgtttcaccg gttggtacga cgtggatctg tctgagaaag gcgtaagcga agcaaaagca     120
gcaggtaagc tgctgaaaga ggaaggttac agctttgact ttgcttacac ttctgtgctg     180
aaacgcgcta tccatacccct gtggaatgtg ctggacgaac tggatcaggc atggctgccc     240
gttgagaaat cctggaaact gaacgaacgt cactacggtg cgttgcaggg tctgaacaaa     300
gcggaaactg ctgaaaagta tggcgacgag caggtgaaac agtggcgtcg tggttttgca     360
gtgactccgc cggaactgac taagatgat gagcgttatc cggtcacga tccgcgttac     420 gcgaaactga gcgagaaaga actgccgctg acggaaagcc tggcgctgac cattgaccgc     480 gtgatcccctt actggaatga actattctg ccgcgtatga agagcggtga gcgcgtgatc     540
atcgctgcac acgtaactc tttacgtgcg ctggtgaaat atcttgataa catgagcgaa     600
gaagagattc ttgagcttaa tatccccgact ggcgtgccgc tggtgtatga gttcgacgag     660
aatttcaaac cgctgaaacg ctattatctg ggtaatgctg acgagatcgc agcgaaagca     720
gcggcggttg caaaccaggg taaagcgaag taa                                  753

<210> SEQ ID NO 16
<211> LENGTH: 250
<212> TYPE: PRT
<213> ORGANISM: Escherichia coli
<220> FEATURE:
<223> OTHER INFORMATION: 2,3-bisphosphoglycerate-dependent
      phosphoglycerate mutase

<400> SEQUENCE: 16

Met Ala Val Thr Lys Leu Val Leu Val Arg His Gly Glu Ser Gln Trp
1               5                   10                  15

Asn Lys Glu Asn Arg Phe Thr Gly Trp Tyr Asp Val Asp Leu Ser Glu
            20                  25                  30

Lys Gly Val Ser Glu Ala Lys Ala Ala Gly Lys Leu Leu Lys Glu Glu
        35                  40                  45

Gly Tyr Ser Phe Asp Phe Ala Tyr Thr Ser Val Leu Lys Arg Ala Ile
    50                  55                  60

His Thr Leu Trp Asn Val Leu Asp Glu Leu Asp Gln Ala Trp Leu Pro
65                  70                  75                  80

Val Glu Lys Ser Trp Lys Leu Asn Glu Arg His Tyr Gly Ala Leu Gln
                85                  90                  95

Gly Leu Asn Lys Ala Glu Thr Ala Glu Lys Tyr Gly Asp Glu Gln Val
            100                 105                 110

Lys Gln Trp Arg Arg Gly Phe Ala Val Thr Pro Pro Glu Leu Thr Lys
        115                 120                 125

Asp Asp Glu Arg Tyr Pro Gly His Asp Pro Arg Tyr Ala Lys Leu Ser
    130                 135                 140

Glu Lys Glu Leu Pro Leu Thr Glu Ser Leu Ala Leu Thr Ile Asp Arg
145                 150                 155                 160

Val Ile Pro Tyr Trp Asn Glu Thr Ile Leu Pro Arg Met Lys Ser Gly
                165                 170                 175

Glu Arg Val Ile Ile Ala Ala His Gly Asn Ser Leu Arg Ala Leu Val
            180                 185                 190

Lys Tyr Leu Asp Asn Met Ser Glu Glu Ile Leu Glu Leu Asn Ile
        195                 200                 205

Pro Thr Gly Val Pro Leu Val Tyr Glu Phe Asp Glu Asn Phe Lys Pro
    210                 215                 220

Leu Lys Arg Tyr Tyr Leu Gly Asn Ala Asp Glu Ile Ala Ala Lys Ala
225                 230                 235                 240

Ala Ala Val Ala Asn Gln Gly Lys Ala Lys
                245                 250

<210> SEQ ID NO 17
<211> LENGTH: 1545
<212> TYPE: DNA
<213> ORGANISM: Escherichia coli
<220> FEATURE:
<223> OTHER INFORMATION: 2,3-bisphosphoglycerate-independent
    phosphoglycerate mutase

<400> SEQUENCE: 17
atgttggttt ctaaaaaacc tatggtactg gtgattctgg atggctatgg ctatcgcgaa      60
gaacagcagg ataacgccat ttttagtgct aaaaccccgg taatggatgc actgtgggcc     120
aatcgtccgc ataccctaat cgacgcttcc ggtctggaag tcggtctgcc tgaccgtcag     180
atgggtaact ccgaagtagg ccacgttaac ctgggtgccg ccgcatcgt gtatcaggac      240 ctgactcgtc tggacgttga aatcaaagat cgcgctttct tgctaatcc ggtgctgact     300 ggcgcggtag ataaagcgaa aaacgcaggc aaagcggtac acattatggg tctgctctcc     360
gcaggcggcg tacacagcca cgaagatcac atcatggcga tggtagaact ggcagctgaa     420
cgcggcgcag aaaaaatcta cctgcacgca ttccttgacg tcgcgacac tccgccgcgc     480 agtgctgaat cctcgctgaa aaaattcgaa gaaaaatttg ccgcgctggg caaaggccgc     540

-continued

```
gtagcgtcca tcattggtcg ttactacgcg atggaccgcg ataaccgttg ggatcgcgta      600
gaaaaagctt atgacctgct gactctggcg cagggcgagt tccaggccga taccgccgtt      660
gctggtttgc aggctgctta tgctcgcgac gaaaatgatg aattcgtgaa agcgaccgtt      720
atccgtgctg aaggtcagcc agacgcggca atggaagacg gcgatgcact gattttcatg      780
aacttccgtg ctgaccgcgc gcgtgaaatc actcgtgctt cgtgaacgc tgatttcgat       840 ggcttcgcgc gtaagaaagt ggttaacgtc gatttcgtga tgctgaccga atacgccgct      900
gacatcaaaa ctgcggttgc ttacccaccc gcttccctgg ttaacacctt cggcgagtgg      960
atggcgaaaa acgacaaaac tcagttgcgt atttccgaaa ccgaaaaata tgcccacgtt     1020
actttcttct tcaacggtgg cgtagaagag tcgttcaaag gcgaagatcg cattctgatc     1080
aactcaccga agtggctac ctacgatctg caaccggaaa tgagctccgc agagctgacc      1140 gaaaactgg ttgcggccat caagagcggc aaatacgaca ccatcatctg taactatccg      1200
aacggcgaca tggtaggtca caccggggtg atggaagcgg cggttaaagc ggttgaagcg     1260
ctggatcact gcgtggaaga agtcgcgaaa gcggttgagt ccgtgggtgg acaactgctg     1320
atcaccgctg accacggtaa cgctgagcag atgcgcgatc cggcaacggg tcaggcacac     1380
acggcacaca ccaacctgcc agttccgctg atttacgttg gtgataagaa cgtgaaagcg     1440
gttgaaggcg gcaaactttc tgacatcgcg ccgaccatgt tgtcgctgat gggtatggaa     1500
atcccgcaag agatgactgg taagccgctg ttcatcgtgg aataa                      1545
```

<210> SEQ ID NO 18
<211> LENGTH: 510
<212> TYPE: PRT
<213> ORGANISM: Escherichia coli
<220> FEATURE:
<223> OTHER INFORMATION: 2,3-bisphosphoglycerate-independent
      phosphoglycerate mutase

<400> SEQUENCE: 18

```
Met Leu Val Ser Lys Lys Pro Met Val Leu Val Ile Leu Asp Gly Tyr
1               5                   10                  15

Gly Tyr Arg Glu Glu Gln Gln Asp Asn Ala Ile Phe Ser Ala Lys Thr
            20                  25                  30

Pro Val Met Asp Ala Leu Trp Ala Asn Arg Pro His Thr Leu Ile Asp
        35                  40                  45

Ala Ser Gly Leu Glu Val Gly Leu Pro Asp Arg Gln Met Gly Asn Ser
    50                  55                  60

Glu Val Gly His Val Asn Leu Gly Ala Gly Arg Ile Val Tyr Gln Asp
65                  70                  75                  80

Leu Thr Arg Leu Asp Val Glu Ile Lys Asp Arg Ala Phe Phe Ala Asn
                85                  90                  95

Pro Val Leu Thr Gly Ala Val Asp Lys Ala Lys Asn Ala Gly Lys Ala
            100                 105                 110

Val His Ile Met Gly Leu Leu Ser Ala Gly Gly Val His Ser His Glu
        115                 120                 125

Asp His Ile Met Ala Met Val Glu Leu Ala Ala Glu Arg Gly Ala Glu
    130                 135                 140

Lys Ile Tyr Leu His Ala Phe Leu Asp Gly Arg Asp Thr Pro Pro Arg
145                 150                 155                 160

Ser Ala Glu Ser Ser Leu Lys Lys Phe Glu Glu Lys Phe Ala Ala Leu
                165                 170                 175
```

-continued

```
Gly Lys Gly Arg Val Ala Ser Ile Ile Gly Arg Tyr Tyr Ala Met Asp
                180                 185                 190

Arg Asp Asn Arg Trp Asp Arg Val Glu Lys Ala Tyr Asp Leu Leu Thr
            195                 200                 205

Leu Ala Gln Gly Glu Phe Gln Ala Asp Thr Ala Val Ala Gly Leu Gln
        210                 215                 220

Ala Ala Tyr Ala Arg Asp Glu Asn Asp Glu Phe Val Lys Ala Thr Val
225                 230                 235                 240

Ile Arg Ala Glu Gly Gln Pro Asp Ala Ala Met Glu Asp Gly Asp Ala
                245                 250                 255

Leu Ile Phe Met Asn Phe Arg Ala Asp Arg Ala Arg Glu Ile Thr Arg
            260                 265                 270

Ala Phe Val Asn Ala Asp Phe Asp Gly Phe Ala Arg Lys Lys Val Val
        275                 280                 285

Asn Val Asp Phe Val Met Leu Thr Glu Tyr Ala Ala Asp Ile Lys Thr
    290                 295                 300

Ala Val Ala Tyr Pro Pro Ala Ser Leu Val Asn Thr Phe Gly Glu Trp
305                 310                 315                 320

Met Ala Lys Asn Asp Lys Thr Gln Leu Arg Ile Ser Glu Thr Glu Lys
                325                 330                 335

Tyr Ala His Val Thr Phe Phe Asn Gly Val Glu Glu Ser Phe
            340                 345                 350

Lys Gly Glu Asp Arg Ile Leu Ile Asn Ser Pro Lys Val Ala Thr Tyr
        355                 360                 365

Asp Leu Gln Pro Glu Met Ser Ser Ala Glu Leu Thr Glu Lys Leu Val
    370                 375                 380

Ala Ala Ile Lys Ser Gly Lys Tyr Asp Thr Ile Ile Cys Asn Tyr Pro
385                 390                 395                 400

Asn Gly Asp Met Val Gly His Thr Gly Val Met Glu Ala Ala Val Lys
                405                 410                 415

Ala Val Glu Ala Leu Asp His Cys Val Glu Val Ala Lys Ala Val
            420                 425                 430

Glu Ser Val Gly Gly Gln Leu Leu Ile Thr Ala Asp His Gly Asn Ala
        435                 440                 445

Glu Gln Met Arg Asp Pro Ala Thr Gly Gln Ala His Thr Ala His Thr
    450                 455                 460

Asn Leu Pro Val Pro Leu Ile Tyr Val Gly Asp Lys Asn Val Lys Ala
465                 470                 475                 480

Val Glu Gly Gly Lys Leu Ser Asp Ile Ala Pro Thr Met Leu Ser Leu
                485                 490                 495

Met Gly Met Glu Ile Pro Gln Glu Met Thr Gly Lys Pro Leu
            500                 505                 510
```

<210> SEQ ID NO 19
<211> LENGTH: 1227
<212> TYPE: DNA
<213> ORGANISM: Escherichia coli
<220> FEATURE:
<223> OTHER INFORMATION: Glycerate-2-kinase

<400> SEQUENCE: 19

```
atggcgtatt gcaatccggg cctggaatcc aggccgaata agagaaacgc cctccggcgt      60
catgtggtaa caggcatagg tatgaaaatc gtaatcgccc cagactctta taaagaaagt     120
ttatctgcca gcgaggttgc gcaggcgata gaaaaggat tcgggaaat ttttcctgat      180
```

-continued

```
gcacagtacg tttctgttcc ggttgccgac ggtggcgaag gaacggtgga agcgatgatt      240
gcagccaccc aggggctga acgtcacgcc tgggttacag ggccgctggg cgagaaagtg      300
aatgccagtt gggggatctc cggcgatggc aaaaccgcgt ttattgaaat ggcggcggcc      360
agtgggctgg agctggtacc tgcggaaaaa cgcgatccac tcgtgaccac ttcacgcggc      420
acaggcgagt taatcctgca ggcgctggag agcggtgcga caaacattat tatcggcatt      480
ggcggcagcg ctacaaatga tggcggcgca ggcatggtac aggcgctggg ggcgaaatta      540
tgcgacgcca acggcaatga aattggtttt ggcggcggta gtcttaatac tctgaatgat      600
attgatattt ccggcctcga tccgcgctta aagattgcg tcattcgcgt cgcttgtgat      660
gtcaccaatc cgctggtggg cgataacggc gcatcgcgca tctttggccc acaaaaggga      720
gccagtgaag cgatgattgt tgagctggac aataacctct ctcactatgc cgaggtcatt      780
aaaaaagcgc tgcatgttga tgtgaaagat gtccccggtg caggagctgc gggtggtatg      840
ggcgcggcgc taatggcgtt tcttggtgcg gaactgaaaa gtggtattga aatcgtcact      900
acggcgctga atctggagga acatattcac gattgtacgc tggtgatcac cggtgaaggg      960
cgtattgaca gccagagtat tcacgggaag gtaccgattg gtgtcgcaaa cgtggcgaag     1020
aagtaccata aaccggtgat tggcattgcg ggtagcctga ccgatgatgt tggcgttgta     1080
catcagcatg gcattgatgc ggtcttcagc gtattgacca gcataggtac gttggacgaa     1140
gcattccgcg gggcttatga caatatctgc cgtgcttcac gtaatatcgc cgcgacactg     1200
gcgattggaa tgcgcaacgc ggggtga                                         1227
```

<210> SEQ ID NO 20
<211> LENGTH: 408
<212> TYPE: PRT
<213> ORGANISM: Escherichia coli
<220> FEATURE:
<223> OTHER INFORMATION: Glycerate-2-kinase

<400> SEQUENCE: 20

```
Met Ala Tyr Cys Asn Pro Gly Leu Glu Ser Arg Pro Asn Lys Arg Asn
1               5                   10                  15

Ala Leu Arg Arg His Val Val Thr Gly Ile Gly Met Lys Ile Val Ile
            20                  25                  30

Ala Pro Asp Ser Tyr Lys Glu Ser Leu Ser Ala Ser Glu Val Ala Gln
        35                  40                  45

Ala Ile Glu Lys Gly Phe Arg Glu Ile Phe Pro Asp Ala Gln Tyr Val
    50                  55                  60

Ser Val Pro Val Ala Asp Gly Gly Glu Gly Thr Val Glu Ala Met Ile
65                  70                  75                  80

Ala Ala Thr Gln Gly Ala Glu Arg His Ala Trp Val Thr Gly Pro Leu
                85                  90                  95

Gly Glu Lys Val Asn Ala Ser Trp Gly Ile Ser Gly Asp Gly Lys Thr
            100                 105                 110

Ala Phe Ile Glu Met Ala Ala Ala Ser Gly Leu Glu Leu Val Pro Ala
        115                 120                 125

Glu Lys Arg Asp Pro Leu Val Thr Thr Ser Arg Gly Thr Gly Glu Leu
    130                 135                 140

Ile Leu Gln Ala Leu Glu Ser Gly Ala Thr Asn Ile Ile Ile Gly Ile
145                 150                 155                 160

Gly Gly Ser Ala Thr Asn Asp Gly Gly Ala Gly Met Val Gln Ala Leu
                165                 170                 175
```

Gly Ala Lys Leu Cys Asp Ala Asn Gly Asn Glu Ile Gly Phe Gly Gly
            180                 185                 190

Gly Ser Leu Asn Thr Leu Asn Asp Ile Asp Ile Ser Gly Leu Asp Pro
        195                 200                 205

Arg Leu Lys Asp Cys Val Ile Arg Val Ala Cys Asp Val Thr Asn Pro
    210                 215                 220

Leu Val Gly Asp Asn Gly Ala Ser Arg Ile Phe Gly Pro Gln Lys Gly
225                 230                 235                 240

Ala Ser Glu Ala Met Ile Val Glu Leu Asp Asn Asn Leu Ser His Tyr
                245                 250                 255

Ala Glu Val Ile Lys Lys Ala Leu His Val Asp Val Lys Asp Val Pro
            260                 265                 270

Gly Ala Gly Ala Ala Gly Gly Met Gly Ala Ala Leu Met Ala Phe Leu
        275                 280                 285

Gly Ala Glu Leu Lys Ser Gly Ile Glu Ile Val Thr Thr Ala Leu Asn
290                 295                 300

Leu Glu Glu His Ile His Asp Cys Thr Leu Val Ile Thr Gly Glu Gly
305                 310                 315                 320

Arg Ile Asp Ser Gln Ser Ile His Gly Lys Val Pro Ile Gly Val Ala
                325                 330                 335

Asn Val Ala Lys Lys Tyr His Lys Pro Val Ile Gly Ile Ala Gly Ser
            340                 345                 350

Leu Thr Asp Asp Val Gly Val His Gln His Gly Ile Asp Ala Val
        355                 360                 365

Phe Ser Val Leu Thr Ser Ile Gly Thr Leu Asp Glu Ala Phe Arg Gly
    370                 375                 380

Ala Tyr Asp Asn Ile Cys Arg Ala Ser Arg Asn Ile Ala Ala Thr Leu
385                 390                 395                 400

Ala Ile Gly Met Arg Asn Ala Gly
                405

<210> SEQ ID NO 21
<211> LENGTH: 1284
<212> TYPE: DNA
<213> ORGANISM: Methylococcus capsulatus
<220> FEATURE:
<223> OTHER INFORMATION: Enolase

<400> SEQUENCE: 21

```
atgagcaaga tcgtcgacat cctggcccgg gagattctgg actcccgcgg caatccgacc        60
gtccaggcgg aagtgatcct ggattcgggc gcggaaggta cgccatggt tccctccggc       120
gcctccaccg cgcccgcga agccatcgaa ctgcgcgacg cgacgcctc acgctatggc        180
ggaaaaggcg tactcaaagc cgtggagaac gtccgcggtc cgatcaaggc cgcactgacc       240
ggcatggacg ccgccgacca ggcggccatc gaccggcgcc tgatcgagct ggatggcagt       300
gacaacaagg gcgtgctcgg cgccaacgcc atcctggcag tgtcgctggc gaccgcccac       360
gctgccgcgg ccgacgcgaa aaagccgctg tacgcctacc tcaaccgcag cggcgaattc       420
ctgctgccgg tgccgatgat gaacatcatc aacggcggcg cccatgccga acagcatc       480
gacatgcagg agttcatgat cctgccggtg ggcgcgccga gcttccgcga agccctgcgc       540
tacggcgcag aagtgttcca cgccctgaag aaagtgctgt cggaccgggg gctcgccacc       600
ggcgtgggtg acgaaggcgg cttcgcgccg aacctgccgt ccaacgaagc agccatcggc       660
atcatcctgg aagccatcga aaaggccggc taccggcccg cgaggacat ctgcctgggt       720
```

```
ctggacgtcg ccagctcgga gttctattcg acggcatct acactctagc ttcggaaggc      780
aggcggttca cctcggaaga gttctcggac catctggccg cctgggtcga caagtacccc      840
atcgtcagca tcgaggacgg catggcggag aacgactggc acggctgggg catccatacc      900
gacaggctgg gccgacgcat ccagttggtg ggcgacgacc tgttcgtgac caacccggcc      960
atcctcaaac agggcatcga agcccggatc gccaattcga tcctgatcaa ggtcaaccag     1020
atcggcaccc tgaccgaaac cctggaagcc atccatatcg ccaggaaggc cggctacacg     1080
tctgtcgtgt cccatcgctc gggcgaaacg gagggcacca ccatcgccga catcgccgtc     1140
gccacctgca ccggccagat caagaccggc tcgctcagcc gctccgatcg catcgccaaa     1200
tacaaccggc tgctcaagat cgaggaagag ctgggtgaca agcgcgcta cggcggccgc     1260 ggcgccgtca aaaacctggc ctga                                           1284
```

<210> SEQ ID NO 22
<211> LENGTH: 427
<212> TYPE: PRT
<213> ORGANISM: Methylococcus capsulatus
<220> FEATURE:
<223> OTHER INFORMATION: Enolase

<400> SEQUENCE: 22

```
Met Ser Lys Ile Val Asp Ile Leu Ala Arg Glu Ile Leu Asp Ser Arg
1               5                   10                  15

Gly Asn Pro Thr Val Gln Ala Glu Val Ile Leu Asp Ser Gly Ala Glu
            20                  25                  30

Gly Ser Ala Met Val Pro Ser Gly Ala Ser Thr Gly Ala Arg Glu Ala
        35                  40                  45

Ile Glu Leu Arg Asp Gly Asp Ala Ser Arg Tyr Gly Gly Lys Gly Val
    50                  55                  60

Leu Lys Ala Val Glu Asn Val Arg Gly Pro Ile Lys Ala Ala Leu Thr
65                  70                  75                  80

Gly Met Asp Ala Ala Asp Gln Ala Ala Ile Asp Arg Arg Leu Ile Glu
                85                  90                  95

Leu Asp Gly Ser Asp Asn Lys Gly Val Leu Gly Ala Asn Ala Ile Leu
            100                 105                 110

Ala Val Ser Leu Ala Thr Ala His Ala Ala Ala Asp Ala Lys Lys
        115                 120                 125

Pro Leu Tyr Ala Tyr Leu Asn Arg Ser Gly Glu Phe Leu Leu Pro Val
    130                 135                 140

Pro Met Met Asn Ile Ile Asn Gly Gly Ala His Ala Asp Asn Ser Ile
145                 150                 155                 160

Asp Met Gln Glu Phe Met Ile Leu Pro Val Gly Ala Pro Ser Phe Arg
                165                 170                 175

Glu Ala Leu Arg Tyr Gly Ala Glu Val Phe His Ala Leu Lys Lys Val
            180                 185                 190

Leu Ser Asp Arg Gly Leu Ala Thr Gly Val Gly Asp Glu Gly Gly Phe
        195                 200                 205

Ala Pro Asn Leu Pro Ser Asn Glu Ala Ala Ile Gly Ile Ile Leu Glu
    210                 215                 220

Ala Ile Glu Lys Ala Gly Tyr Arg Pro Gly Glu Asp Ile Cys Leu Gly
225                 230                 235                 240

Leu Asp Val Ala Ser Ser Glu Phe Tyr Ser Asp Gly Ile Tyr Thr Leu
                245                 250                 255

Ala Ser Glu Gly Arg Arg Phe Thr Ser Glu Glu Phe Ser Asp His Leu
```

```
                260             265              270
Ala Ala Trp Val Asp Lys Tyr Pro Ile Val Ser Ile Glu Asp Gly Met
            275                 280             285

Ala Glu Asn Asp Trp His Gly Trp Gly Ile His Thr Asp Arg Leu Gly
            290                 295             300

Arg Arg Ile Gln Leu Val Gly Asp Asp Leu Phe Val Thr Asn Pro Ala
305             310              315             320

Ile Leu Lys Gln Gly Ile Glu Ala Arg Ile Ala Asn Ser Ile Leu Ile
                325             330             335

Lys Val Asn Gln Ile Gly Thr Leu Thr Glu Thr Leu Glu Ala Ile His
            340             345             350

Ile Ala Arg Lys Ala Gly Tyr Thr Ser Val Val Ser His Arg Ser Gly
            355             360             365

Glu Thr Glu Gly Thr Thr Ile Ala Asp Ile Ala Val Ala Thr Cys Thr
            370             375             380

Gly Gln Ile Lys Thr Gly Ser Leu Ser Arg Ser Asp Arg Ile Ala Lys
385             390             395             400

Tyr Asn Arg Leu Leu Lys Ile Glu Glu Glu Leu Gly Asp Lys Ala Arg
                405             410             415

Tyr Gly Gly Arg Gly Ala Val Lys Asn Leu Ala
            420             425
```

```
<210> SEQ ID NO 23
<211> LENGTH: 1011
<212> TYPE: DNA
<213> ORGANISM: Methylococcus capsulatus
<220> FEATURE:
<223> OTHER INFORMATION: Glyceraldehye 3-phosphate dehydrogenase

<400> SEQUENCE: 23
atgacgatta agattgcaat caatggatat gggcgcatcg gccgcaacat cctgcgggcg     60
atttacgaaa ccgggcgcaa ggatgtggag atcgtcgcca tcaatgacct ggggatgcc    120
cagatcaacg cccatctcac ccgccatgac accgtgcacg gccgttccg ggggaccgtg    180
gaggtcggcg agggcgaaat catcgtcaac ggcgaccgca tcagggtttt tccgagaag    240
gatccttcca agctgccctg gggggctttg gcgtggacg tcgtgcatga gtgcaccggg    300
gtgttccgca ccaaggccaa atgccagccg catctcgatg ccggcgccaa gaaggtgatc    360
atttcggccc cggccgacaa gaacgagtgc gacgcgacca tcgtctacgg ggtcaatgag    420
catacgctga agccgcccca caccgtcatc tcgaatgcat cctgcaccac caactgcctg    480
gcgccgctgg tcaagccgct gctgggaaaa atcgggatcg tgtccggcct catgaccacc    540
gtgcattcct acaccaacga ccaggtgctc accgacgttt atcacaagga tctgtaccgg    600
gcacgggcgg cggcgctgaa catgatcccg accaagaccg gcgggcgca ggccgtgggg    660
ctggtgctgc cggagctgga cggcaaactg tccggtttcg ccatccgggt gccgaccgcc    720
aatgtatcgg tcgtggacct gaccttcatc gcggcccggg aaaccgacaa ggacgagatc    780
aacgccatcc tcaaggccgc ttccgaaagc gagctgaagg gtatcctcgg ctacaacgac    840
cagccgctgg tctcgagcga tttcaatcat cgacgactt cctccaattt cgactcgacc    900
cagaccaagg tggtcggcaa cctggtgaag gtgctgagct ggtacgacaa cgagtggggt    960
ttcagcaacc gcatgctgga caccacggtc gccctgatga acgcccgatg a             1011

<210> SEQ ID NO 24
<211> LENGTH: 336
```

<212> TYPE: PRT
<213> ORGANISM: Methylococcus capsulatus
<220> FEATURE:
<223> OTHER INFORMATION: Glyceraldehye 3-phosphate dehydrogenase

<400> SEQUENCE: 24

```
Met Thr Ile Lys Ile Ala Ile Asn Gly Tyr Gly Arg Ile Gly Arg Asn
1               5                   10                  15

Ile Leu Arg Ala Ile Tyr Glu Thr Gly Arg Lys Asp Val Glu Ile Val
            20                  25                  30

Ala Ile Asn Asp Leu Gly Asp Ala Gln Ile Asn Ala His Leu Thr Arg
        35                  40                  45

His Asp Thr Val His Gly Pro Phe Arg Gly Thr Val Glu Val Gly Glu
    50                  55                  60

Gly Glu Ile Ile Val Asn Gly Asp Arg Ile Arg Val Phe Ser Glu Lys
65                  70                  75                  80

Asp Pro Ser Lys Leu Pro Trp Gly Ala Leu Gly Val Asp Val Val His
                85                  90                  95

Glu Cys Thr Gly Val Phe Arg Thr Lys Ala Lys Cys Gln Pro His Leu
            100                 105                 110

Asp Ala Gly Ala Lys Lys Val Ile Ile Ser Ala Pro Ala Asp Lys Asn
        115                 120                 125

Glu Cys Asp Ala Thr Ile Val Tyr Gly Val Asn Glu His Thr Leu Lys
    130                 135                 140

Ala Ala His Thr Val Ile Ser Asn Ala Ser Cys Thr Thr Asn Cys Leu
145                 150                 155                 160

Ala Pro Leu Val Lys Pro Leu Leu Gly Lys Ile Gly Ile Val Ser Gly
                165                 170                 175

Leu Met Thr Thr Val His Ser Tyr Thr Asn Asp Gln Val Leu Thr Asp
            180                 185                 190

Val Tyr His Lys Asp Leu Tyr Arg Ala Arg Ala Ala Leu Asn Met
        195                 200                 205

Ile Pro Thr Lys Thr Gly Ala Ala Gln Ala Val Gly Leu Val Leu Pro
    210                 215                 220

Glu Leu Asp Gly Lys Leu Ser Gly Phe Ala Ile Arg Val Pro Thr Ala
225                 230                 235                 240

Asn Val Ser Val Val Asp Leu Thr Phe Ile Ala Ala Arg Glu Thr Asp
                245                 250                 255

Lys Asp Glu Ile Asn Ala Ile Leu Lys Ala Ala Ser Glu Ser Glu Leu
            260                 265                 270

Lys Gly Ile Leu Gly Tyr Asn Asp Gln Pro Leu Val Ser Ser Asp Phe
        275                 280                 285

Asn His Thr Thr Thr Ser Ser Asn Phe Asp Ser Thr Gln Thr Lys Val
    290                 295                 300

Val Gly Asn Leu Val Lys Val Leu Ser Trp Tyr Asp Asn Glu Trp Gly
305                 310                 315                 320

Phe Ser Asn Arg Met Leu Asp Thr Thr Val Ala Leu Met Asn Ala Arg
                325                 330                 335
```

<210> SEQ ID NO 25
<211> LENGTH: 693
<212> TYPE: DNA
<213> ORGANISM: Methylococcus capsulatus
<220> FEATURE:
<223> OTHER INFORMATION: Ribulose phosphate 3-epimerase

<400> SEQUENCE: 25

```
atgaacgaat tctggatcgc cccctcgatt ctctccgccg acttcgcccg tctcggcgag    60
gaagtggacg acgtcctcaa gtcgggcgcc gacatcgtcc atttcgacgt gatggacaac   120
cactacgtcc cgaacctgac catcggcccg ctggtgtgcg aggcattgcg caagcacggc   180
gtgaccgcgc cgatcgacgt gcacctgatg gtcaagccgg tcgaccgcat cattcccgat   240
ttcgccaagg ccggggccag ctacatcacc ttccatccgg aggcctccga gcacatcgac   300
cgcagcctgc aactcgtcaa ggactccggc tgcaagaccg gctggtgtt caatccggcc   360
acaccgctca actatctgga tcacgtcatg acaagctcg acatgatcct gctgatgtcg   420
gtcaaccccg gcttcggcgg ccaatccttc atcccctacg tgctggacaa ggtccgcgag   480
tgccgccgcc gcatcgacgc cagcggccgc aacatccgcc tggagatcga cggcggcgtc   540
aacgccagga acatccgcga gatcgccgcc gcgggctgcg acaccttcgt cgccggctcg   600
gcggtgttcg gcgcgggcaa ggccgaagat ccgaaccgct acgactccat catccgcgcc   660
ctgcgcgacg aactggccca gacccgcgca tga                                693
```

```
<210> SEQ ID NO 26
<211> LENGTH: 230
<212> TYPE: PRT
<213> ORGANISM: Methylococcus capsulatus
<220> FEATURE:
<223> OTHER INFORMATION: Ribulose phosphate 3-epimerase

<400> SEQUENCE: 26

Met Asn Glu Phe Trp Ile Ala Pro Ser Ile Leu Ser Ala Asp Phe Ala
1               5                   10                  15

Arg Leu Gly Glu Glu Val Asp Asp Val Leu Lys Ser Gly Ala Asp Ile
            20                  25                  30

Val His Phe Asp Val Met Asp Asn His Tyr Val Pro Asn Leu Thr Ile
        35                  40                  45

Gly Pro Leu Val Cys Glu Ala Leu Arg Lys His Gly Val Thr Ala Pro
    50                  55                  60

Ile Asp Val His Leu Met Val Lys Pro Val Arg Ile Ile Pro Asp
65                  70                  75                  80

Phe Ala Lys Ala Gly Ala Ser Tyr Ile Thr Phe His Pro Glu Ala Ser
                85                  90                  95

Glu His Ile Asp Arg Ser Leu Gln Leu Val Lys Asp Ser Gly Cys Lys
            100                 105                 110

Thr Gly Leu Val Phe Asn Pro Ala Thr Pro Leu Asn Tyr Leu Asp His
        115                 120                 125

Val Met Asp Lys Leu Asp Met Ile Leu Leu Met Ser Val Asn Pro Gly
130                 135                 140

Phe Gly Gly Gln Ser Phe Ile Pro Tyr Val Leu Asp Lys Val Arg Glu
145                 150                 155                 160

Cys Arg Arg Arg Ile Asp Ala Ser Gly Arg Asn Ile Arg Leu Glu Ile
                165                 170                 175

Asp Gly Gly Val Asn Ala Arg Asn Ile Arg Glu Ile Ala Ala Ala Gly
            180                 185                 190

Cys Asp Thr Phe Val Ala Gly Ser Ala Val Phe Gly Ala Gly Lys Ala
        195                 200                 205

Glu Asp Pro Asn Arg Tyr Asp Ser Ile Ile Arg Ala Leu Arg Asp Glu
    210                 215                 220

Leu Ala Gln Thr Arg Ala
225                 230
```

<210> SEQ ID NO 27
<211> LENGTH: 1860
<212> TYPE: DNA
<213> ORGANISM: Methylococcus capsulatus
<220> FEATURE:
<223> OTHER INFORMATION: Methanol dehydrogenase larger subunit

<400> SEQUENCE: 27

| | | | | | | |
|---|---|---|---|---|---|---|
| atgaaaaaac | ccgtgaaaag | ctggctcatc | gcaagttcca | tagcatcgtt | gctggcagta | 60 |
| cccggggtct | ctttcgcgaa | cgctgaagtg | aagcactca | ccaaggatcc | gaagaacttt | 120 |
| gcgacttggg | gtggcaacta | cgcgggcacg | cgttacagca | cgctggacca | gatcaatttc | 180 |
| aagaacgcca | agcatctgca | gccggtctgg | acgttctcca | cgggcatgct | gcgcggccat | 240 |
| gaaggcggtc | cgctcgtcgt | caacgacgtg | atctacattc | ataccgggta | tcccacaag | 300 |
| gtctacgccc | tcgatcaggc | gactcagtcc | gtgatctggg | aatatgtcta | tgctcccgac | 360 |
| aagggcaccg | atcagtcaca | ggtcatttcc | gtgatgtgct | gcgacgtggt | caaccgcggt | 420 |
| ctggcctacg | gtgacggcaa | gatcttcctg | gcccagggcg | acgctacgct | ggtggccctc | 480 |
| gacgccaaga | ccggcaagat | cgtctggaaa | gtcaagaacg | gcgatccgaa | gaccggcatg | 540 |
| accgccacca | acgccccct | ggtcgtcaag | gacaaggtcc | tgaccggtat | ctccggtggt | 600 |
| gaattcggcg | tgcgcggctt | cctggctgct | tataacatca | aggacggttc | gctggtatgg | 660 |
| aagaagtaca | gcatgggtcc | ggatgacgag | gtcggcctgg | atcccgagca | caccatgacc | 720 |
| tggaccgatg | gcaaaatggc | gccggtcggc | aaggattcct | cgctgaagac | ctggcaaggc | 780 |
| gaccagtgga | aaatcggcgg | cggtaccacc | tggggctggt | acagctacga | cccggatctg | 840 |
| aatctggttt | actacggttc | gggcaacccc | agcacctgga | accggtgca | gcgtcctggc | 900 |
| gacaacaaat | ggtcgatgac | catctgggct | cgtgacgtcg | ataccggtga | agccaagtgg | 960 |
| gtctaccaga | tgaccccgca | tgacgaatgg | gactatgacg | gcatcaacga | atgatgctg | 1020 |
| atcgaccagg | aaatgaccgc | gaaggacgga | tccaagcact | ccaagctgct | gacccacttc | 1080 |
| gaccgtaacg | gctttggcta | cacccctgac | cgcgtcaccg | gcgagctgct | ggtggccgag | 1140 |
| aagttcgaca | aggccgtcaa | ctgggcgact | cacgtcgaca | tgaagacggg | ccgtccgcag | 1200 |
| gtcaatccga | gtactccac | ccagcatggc | ggccaggacg | tcgacaccaa | gggcatctgc | 1260 |
| ccctcggcca | tggcgccaa | gaacgagccc | ccggtcactt | actcgccgcg | gaccaagctc | 1320 |
| atctacatcc | cgggtaacca | cacctgcatg | aactatgagc | cgttcgaggt | cgaatacacc | 1380 |
| gcaggccagc | cgtatgtcgg | cgccacgctg | aacatcttcc | cggccagggc | caacgtgaaa | 1440 |
| accggcgaga | aggaatcgag | caaccacatg | gggtccttca | ccgcctggga | tccgaccacc | 1500 |
| ggtaccatcg | cctggcagtt | cgacgaaccc | ttctcgctgt | ggagcggcat | ggtttcgacc | 1560 |
| gccggcgaca | tcgtgattta | cggtacgctg | gaaggctacc | tgaaggtgcg | cgatgccaag | 1620 |
| accggtgagg | aactgtaccg | gttcaagacg | ccgtcgggca | tcatcggcaa | cgtcagcacc | 1680 |
| tggacctaca | acggcaagca | gtacatcggc | gtgctgtccg | gcatcggtgg | ctgggctggc | 1740 |
| gtgggcatgg | cggccggtct | ggaaggtgat | accgaaggtc | tgggtgcggt | gggtgcctac | 1800 |
| aagggtctga | gcagccatac | caagctgggt | ggtgtgttca | ccgtgttcgc | tctgccgtaa | 1860 |

<210> SEQ ID NO 28
<211> LENGTH: 619
<212> TYPE: PRT
<213> ORGANISM: Methylococcus capsulatus
<220> FEATURE:

<223> OTHER INFORMATION: Methanol dehydrogenase larger subunit

<400> SEQUENCE: 28

```
Met Lys Lys Pro Val Lys Ser Trp Leu Ile Ala Ser Ser Ile Ala Ser
1               5                   10                  15

Leu Leu Ala Val Pro Gly Val Ser Phe Ala Asn Ala Glu Val Glu Ala
            20                  25                  30

Leu Thr Lys Asp Pro Lys Asn Phe Ala Thr Trp Gly Gly Asn Tyr Ala
        35                  40                  45

Gly Thr Arg Tyr Ser Thr Leu Asp Gln Ile Asn Phe Lys Asn Ala Lys
    50                  55                  60

His Leu Gln Pro Val Trp Thr Phe Ser Thr Gly Met Leu Arg Gly His
65                  70                  75                  80

Glu Gly Gly Pro Leu Val Val Asn Asp Val Ile Tyr Ile His Thr Gly
                85                  90                  95

Tyr Pro His Lys Val Tyr Ala Leu Asp Gln Ala Thr Gln Ser Val Ile
            100                 105                 110

Trp Glu Tyr Val Tyr Ala Pro Asp Lys Gly Thr Asp Gln Ser Gln Val
        115                 120                 125

Ile Ser Val Met Cys Cys Asp Val Val Asn Arg Gly Leu Ala Tyr Gly
130                 135                 140

Asp Gly Lys Ile Phe Leu Ala Gln Gly Asp Ala Thr Leu Val Ala Leu
145                 150                 155                 160

Asp Ala Lys Thr Gly Lys Ile Val Trp Lys Val Lys Asn Gly Asp Pro
                165                 170                 175

Lys Thr Gly Met Thr Ala Thr Asn Ala Pro Leu Val Val Lys Asp Lys
            180                 185                 190

Val Leu Thr Gly Ile Ser Gly Gly Glu Phe Gly Val Arg Gly Phe Leu
        195                 200                 205

Ala Ala Tyr Asn Ile Lys Asp Gly Ser Leu Val Trp Lys Lys Tyr Ser
    210                 215                 220

Met Gly Pro Asp Asp Glu Val Gly Leu Asp Pro Glu His Thr Met Thr
225                 230                 235                 240

Trp Thr Asp Gly Lys Met Ala Pro Val Gly Lys Asp Ser Ser Leu Lys
                245                 250                 255

Thr Trp Gln Gly Asp Gln Trp Lys Ile Gly Gly Gly Thr Thr Trp Gly
            260                 265                 270

Trp Tyr Ser Tyr Asp Pro Asp Leu Asn Leu Val Tyr Tyr Gly Ser Gly
        275                 280                 285

Asn Pro Ser Thr Trp Asn Pro Val Gln Arg Pro Gly Asp Asn Lys Trp
    290                 295                 300

Ser Met Thr Ile Trp Ala Arg Asp Val Asp Thr Gly Glu Ala Lys Trp
305                 310                 315                 320

Val Tyr Gln Met Thr Pro His Asp Glu Trp Asp Tyr Asp Gly Ile Asn
                325                 330                 335

Glu Met Met Leu Ile Asp Gln Glu Met Thr Ala Lys Asp Gly Ser Lys
            340                 345                 350

His Ser Lys Leu Leu Thr His Phe Asp Arg Asn Gly Phe Gly Tyr Thr
        355                 360                 365

Leu Asp Arg Val Thr Gly Glu Leu Leu Val Ala Glu Lys Phe Asp Lys
    370                 375                 380

Ala Val Asn Trp Ala Thr His Val Asp Met Lys Thr Gly Arg Pro Gln
385                 390                 395                 400
```

Val Asn Pro Lys Tyr Ser Thr Gln His Gly Gln Asp Val Asp Thr
                405                 410                 415

Lys Gly Ile Cys Pro Ser Ala Met Gly Ala Lys Asn Glu Pro Pro Val
            420                 425                 430

Thr Tyr Ser Pro Arg Thr Lys Leu Ile Tyr Ile Pro Gly Asn His Thr
        435                 440                 445

Cys Met Asn Tyr Glu Pro Phe Glu Val Glu Tyr Thr Ala Gly Gln Pro
    450                 455                 460

Tyr Val Gly Ala Thr Leu Asn Ile Phe Pro Ala Arg Ala Asn Val Lys
465                 470                 475                 480

Thr Gly Glu Lys Glu Ser Ser Asn His Met Gly Ser Phe Thr Ala Trp
                485                 490                 495

Asp Pro Thr Thr Gly Thr Ile Ala Trp Gln Phe Asp Glu Pro Phe Ser
            500                 505                 510

Leu Trp Ser Gly Met Val Ser Thr Ala Gly Asp Ile Val Ile Tyr Gly
        515                 520                 525

Thr Leu Glu Gly Tyr Leu Lys Val Arg Asp Ala Lys Thr Gly Glu Glu
    530                 535                 540

Leu Tyr Arg Phe Lys Thr Pro Ser Gly Ile Ile Gly Asn Val Ser Thr
545                 550                 555                 560

Trp Thr Tyr Asn Gly Lys Gln Tyr Ile Gly Val Leu Ser Gly Ile Gly
                565                 570                 575

Gly Trp Ala Gly Val Gly Met Ala Ala Gly Leu Glu Gly Asp Thr Glu
            580                 585                 590

Gly Leu Gly Ala Val Gly Ala Tyr Lys Gly Leu Ser Ser His Thr Lys
        595                 600                 605

Leu Gly Gly Val Phe Thr Val Phe Ala Leu Pro
    610                 615

<210> SEQ ID NO 29
<211> LENGTH: 285
<212> TYPE: DNA
<213> ORGANISM: Methylococcus capsulatus
<220> FEATURE:
<223> OTHER INFORMATION: Methanol dehydrogenase smaller subunit

<400> SEQUENCE: 29
atgatgcaga aaacgagttt cgtcgcggcc gccatggccg tttcgttcgc ggcgggtgtc      60
caggcctatg acggtaccca ctgcaaggcg cccggaaact gctgggagcc caagcccggt     120
tatccggaca aggtcgccgg cagcaagtac gaccccaagc atgacccgaa cgagctcaac     180
aagcaggcgg agtcgatcaa ggcgatggaa gcccgcaacc agaagcgcgt ggagaactac     240
gccaagaccg gcaagttcgt ctacaaggtc gaagacatca aatga                     285

<210> SEQ ID NO 30
<211> LENGTH: 94
<212> TYPE: PRT
<213> ORGANISM: Methylococcus capsulatus
<220> FEATURE:
<223> OTHER INFORMATION: Methanol dehydrogenase smaller subunit

<400> SEQUENCE: 30

Met Met Gln Lys Thr Ser Phe Val Ala Ala Ala Met Ala Val Ser Phe
1               5                   10                  15

Ala Ala Gly Val Gln Ala Tyr Asp Gly Thr His Cys Lys Ala Pro Gly
            20                  25                  30

Asn Cys Trp Glu Pro Lys Pro Gly Tyr Pro Asp Lys Val Ala Gly Ser

```
                35                  40                  45
Lys Tyr Asp Pro Lys His Asp Pro Asn Glu Leu Asn Lys Gln Ala Glu
    50                  55                  60

Ser Ile Lys Ala Met Glu Ala Arg Asn Gln Lys Arg Val Glu Asn Tyr
65                  70                  75                  80

Ala Lys Thr Gly Lys Phe Val Tyr Lys Val Glu Asp Ile Lys
                85                  90
```